(12) United States Patent
Masuda et al.

(10) Patent No.: US 11,802,181 B2
(45) Date of Patent: Oct. 31, 2023

(54) DI-AMINE COMPOUND, AND HEAT-RESISTANT RESIN AND RESIN COMPOSITION USING THE SAME

(71) Applicant: TORAY INDUSTRIES, INC., Tokyo (JP)

(72) Inventors: Yuki Masuda, Otsu (JP); Ryoji Okuda, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 1207 days.

(21) Appl. No.: 16/343,957

(22) PCT Filed: Aug. 28, 2017

(86) PCT No.: PCT/JP2017/030746
§ 371 (c)(1),
(2) Date: Apr. 22, 2019

(87) PCT Pub. No.: WO2018/087990
PCT Pub. Date: May 17, 2018

(65) Prior Publication Data
US 2019/0256655 A1    Aug. 22, 2019

(30) Foreign Application Priority Data
Nov. 10, 2016    (JP) .................... 2016-219464

(51) Int. Cl.
C08G 69/26    (2006.01)
C08G 73/08    (2006.01)
(Continued)

(52) U.S. Cl.
CPC ............ C08G 69/26 (2013.01); C07C 235/24 (2013.01); C07C 237/04 (2013.01); C08G 73/08 (2013.01);
(Continued)

(58) Field of Classification Search
CPC ...... C08G 69/26; C08G 73/10; C08J 2379/08; C08L 79/08; G03F 7/0387
See application file for complete search history.

(56) References Cited

U.S. PATENT DOCUMENTS

2018/0066107 A1    3/2018    Shoji et al.

FOREIGN PATENT DOCUMENTS

JP    11-199557 A    7/1999
WO    WO 2016/152794 A1    9/2016

OTHER PUBLICATIONS

USPTO structure search, Aug. 2023.*
International Search Report, issued in PCT/JP2017/030746, PCT/ISA/210, dated Sep. 26, 2017.
Written Opinion of the International Searching Authority, issued in PCT/JP2017/030746, PCT/ISA/237, dated Sep. 26, 2017.

* cited by examiner

Primary Examiner — Gregory Listvoyb
(74) Attorney, Agent, or Firm — Birch, Stewart, Kolasch & Birch, LLP

(57) ABSTRACT

The present invention relates to a novel di-amine compound, a heat-resistant resin using the di-amine compound, and a resin composition using the heat-resistant resin, and a cured film excellent in chemical resistance and film properties even by a thermal treatment at a low temperature of 200° C. or less can be obtained. The novel di-amine compound is represented by the general formula (1). The heat-resistant resin composition of the present invention or the resin composition can be suitably used in a surface protective film and an interlayer dielectric film of a semiconductor device, a dielectric layer or a planarizing layer of an organic electroluminescent element (organic EL), or the like.

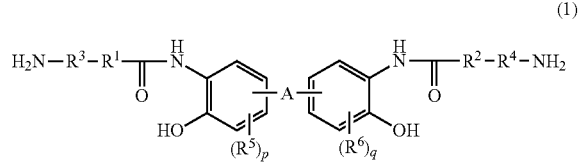

(1)

(In the general formula (1), $R^1$ and $R^2$ each are a divalent aliphatic group, $R^3$ and $R^4$ each are a divalent aliphatic group, aliphatic ring group, aromatic group, a divalent organic group bonded to an aromatic group by —O—, —CO—, —SO$_2$—, —CH$_2$—, —C(CH$_3$)$_2$— or —C(CF$_3$)$_2$— (wherein F is fluorine), a divalent organic group in which two or more aromatic groups are bonded by a single bond, or a divalent organic group in which two or more aromatic groups are bonded by —O—, —CO—, —SO$_2$—, —CH$_2$—, —C(CH$_3$)$_2$— or —C(CF$_3$)$_2$— (wherein F is fluorine), $R^5$ and $R^6$ each are an organic group having any of a hydrogen atom, a halogen atom, a hydroxyl group, a nitro group, a cyano group, an aliphatic group, an aromatic group, an acetyl group, a carboxyl group, an ester group, an amide group, an imide group, and a urea group, A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine), p and q each are an integer number in the range of 0 to 3).

12 Claims, 5 Drawing Sheets

(51) Int. Cl.
*G03F 7/075* (2006.01)
*G03F 7/20* (2006.01)
*H01L 23/29* (2006.01)
*H01L 23/31* (2006.01)
*G03F 7/023* (2006.01)
*H05B 33/02* (2006.01)
*H01L 29/786* (2006.01)
*C07C 237/04* (2006.01)
*H01L 23/12* (2006.01)
*H05B 33/12* (2006.01)
*C07C 235/24* (2006.01)
*H05B 33/22* (2006.01)
*H10K 50/00* (2023.01)
*H10K 59/00* (2023.01)
*C08G 73/10* (2006.01)

(52) U.S. Cl.
CPC .......... *G03F 7/0233* (2013.01); *G03F 7/0751* (2013.01); *G03F 7/2022* (2013.01); *H01L 23/12* (2013.01); *H01L 23/29* (2013.01); *H01L 23/31* (2013.01); *H01L 29/786* (2013.01); *H05B 33/02* (2013.01); *H05B 33/12* (2013.01); *H05B 33/22* (2013.01); *H10K 50/00* (2023.02); *H10K 59/00* (2023.02); *C08G 73/10* (2013.01)

DI-AMINE COMPOUND, AND HEAT-RESISTANT RESIN AND RESIN COMPOSITION USING THE SAME

TECHNICAL FIELD

The present invention relates to a novel di-amine compound, a heat-resistant resin using the di-amine compound, and a resin composition using the heat-resistant resin. More specifically, the present invention relates to a photosensitive resin composition which is suitable in a surface protective film or an interlayer dielectric film of a semiconductor device, a dielectric layer or a flat layer of an organic electroluminescent element (organic EL), or the like.

BACKGROUND ART

Conventionally, polyimide resins, polybenzoxazole resins and the like, which are excellent in heat resistance, mechanical properties and the like, have been widely used in surface protective films, interlayer dielectric films and the like of a semiconductor device of an electronic equipment (Patent Document 1). When a polyimide or a polybenzoxazole is used as a surface protective film or an interlayer dielectric film, one method of forming a through hole or the like is etching in which a positive type photoresist is used. However, this method poses a problem of complexity because a step of applying and removing a photoresist is required. Therefore, a heat-resistant material imparted with photosensitivity has been studied for the purpose of rationalizing the working process (Patent Document 2).

Generally, when a polyimide or a polybenzoxazole is used, a thin film having excellent heat resistance and mechanical properties is obtained by thermally dehydrating and ring-closing a coated film of a precursor of the polyimide or the polybenzoxazole. In this case, a burning at a high temperature of about 350° C. is usually necessary. However, an MRAM (Magnetoresistive Random Access Memory), which is a promising next-generation memory, and an encapsulation resin, for example, are sensitive to high temperatures. Therefore, for the use in a surface protective film of such a device or in an interlayer dielectric film of a fan-out wafer level package forming a rewire structure on an encapsulation resin, a polyimide resin or a polybenzoxazole resin which is cured by burning at a low temperature of about 200° C. or less and can provide characteristics comparable to those obtained by burning a conventional material at a high temperature of about 350° C. has been required.

When a resin composition is used for applications such as semiconductors and the like, physical properties, particularly the degree of elongation, of the cured film are very important because the film after thermal curing remains in the device as a permanent film. When a resin composition is used for applications such as dielectric films between wire layers of a wafer level package, a treatment with a chemical liquid is repeatedly carried out when a metal wire is formed. Thus, chemical resistance to withstand the treatment is required.

In response to these problems, a polybenzoxazole precursor (Patent Document 3) having an aliphatic group and a method of using a photosensitive resin composition containing a novolac resin which has a crosslinking group have been proposed (Patent Document 4).

PRIOR ART REFERENCES

Patent Documents

| PATENT DOCUMENT 1 | JP H11-199557A |
| PATENT DOCUMENT 2 | JP H11-24271A |
| PATENT DOCUMENT 3 | JP2008-224984A |
| PATENT DOCUMENT 4 | JP2011-197362A |

SUMMARY OF THE INVENTION

Problems to be Solved by the Invention

However, the polybenzoxazole precursor having an aliphatic group, especially the polybenzoxazole precursor with a lower curing temperature had a problem of a poor chemical resistance. The photosensitive resin composition containing a novolac resin having a crosslinking group also had a problem of a poor degree of elongation.

The present invention has been achieved in view of the problems accompanying the prior art as described above and provides a resin composition capable of providing a cured film which is excellent in chemical resistance and film properties even by a thermal treatment at a low temperature of 200° C. or less, a heat-resistant resin used in the resin composition, and further a di-amine compound which is a raw material thereof.

Means for Solving the Problems

In order to solve the above problems, the di-amine compound, the heat-resistant resin and the resin composition of the present invention or the application thereof has the following structure.

[1] A di-amine compound represented by the general formula (1).

[Chem 1]

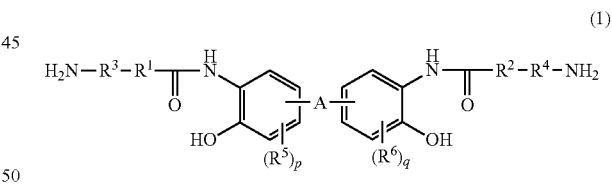

(In the general formula (1), $R^1$ and $R^2$ each are a divalent aliphatic group.

$R^3$ and $R^4$ each are a divalent aliphatic group, aliphatic ring group, aromatic group, a divalent organic group in which an aromatic group is bonded by —O—, —CO—, —$SO_2$—, —$CH_2$—, —$C(CH_3)_2$— or $C(CF_3)_2$—: (wherein F is fluorine), a divalent organic group in which two or more aromatic groups are bonded by a single bond, or a divalent organic group in which two or more aromatic groups are bonded by —O—, —CO—, —$SO_2$—, —$CH_2$—, —$C(CH_3)_2$— or —$C(CF_3)_2$— (wherein F is fluorine).

$R^5$ and $R^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group.

A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine).

p and q each are independently an integer number in the range of 0 to 3).

[2] The di-amine compound according to [1], which is represented by the general formula (1), wherein $R^1$ and $R^2$ in the general formula (1) each are independently a divalent aliphatic group represented by the general formula (2) or the general formula (3).

[Chem 2]

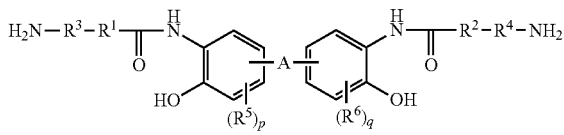

(1)

(In the general formula (1), $R^3$ and $R^4$ each are a divalent aliphatic group, aliphatic ring group, aromatic group, a divalent organic group in which an aromatic group is bonded by —O—, —CO—, —SO$_2$—, —CH$_2$—, —C(CH$_3$)$_2$— or —C(CF$_3$)$_2$— (wherein F is fluorine), a divalent organic group in which two or more aromatic groups are bonded by a single bond, or a divalent organic group in which two or more aromatic groups are bonded by —O—, —CO—, —SO$_2$—, —CH$_2$—, —C(CH$_3$)$_2$— or —C(CF$_3$)$_2$— (wherein F is fluorine).

$R^5$ and $R^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group.

A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine).

p and q each are independently an integer number in the range of 0 to 3).

[Chem 3]

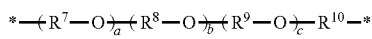

(2)

(In the general formula (2), $R^7$ to $R^{10}$ each are independently a C$_1$-C$_{10}$ alkylene group, and each of a, b and c is an integer number in the range of 1≤a≤20, 0≤b≤20, and 0≤c≤20, and the arrangement of the repeating units may be in a block way or in a random way. * indicates a chemical bond (in other words, an end portion of a divalent group).)

[Chem 4]

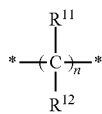

(3)

(In the general formula (3), $R^{11}$ and $R^{12}$ each are independently hydrogen, fluorine, or a C$_1$-C$_6$ alkyl group, and n is an integer number of 1 to 20. * indicates a chemical bond (in other words, an end portion of a divalent group).)

[3] The di-amine compound according to [1] or [2], which is represented by the general formula (1), wherein $R^3$ in the general formula (1) is a divalent organic group represented by the formula (4) and $R^4$ in the general formula (1) is a divalent organic group represented by the formula (5).

[Chem 5]

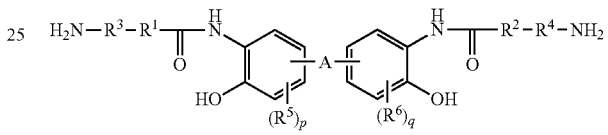

(1)

(In the general formula (1), $R^1$ and $R^2$ each are a divalent aliphatic group.

$R^5$ and $R^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group.

A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine).

p and q each are independently an integer number in the range of 0 to 3).

[Chem 6]

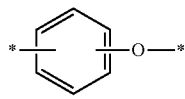

(4)

(In the general formula (4), * indicates a chemical bond (in other words, an end portion of a divalent group).)

[Chem 7]

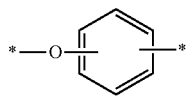

(5)

(In the general formula (5), * indicates a chemical bond (in other words, an end portion of a divalent group).)

[4] A heat-resistant resin having a structure derived from the di-amine compound according to any one of [1] to [3].

[5] The heat-resistant resin according to [4], comprising at least one kind selected from polyimides, polyamides, polybenzoxazoles, polybenzimidazoles, polybenzothiazoles, precursors thereof, and copolymers thereof.

[6] A resin composition comprising the heat-resistant resin according to [4] or [5], (b) a photosensitive compound and (c) a solvent.

[7] The resin composition according to [6], further comprising (d) a compound having two or more of at least one of an alkoxymethyl group and a methylol group.

[8] A resin sheet formed of the resin composition according to [6] or [7].

[9] A cured film obtained by curing the resin composition according to [6] or [7].

[10] A cured film obtained by curing the resin sheet according to [8].

[11] A method of producing a relief pattern of a cured film, comprising the steps of coating the resin composition according to [6] or [7] on a substrate or laminating the resin sheet according to [8] on a substrate, and drying the resin composition or the resin sheet to form a resin film, exposing the resin film through a mask,
eluting or removing irradiated portion by an alkali solution to develop the resin film, and
thermally treating the resin film after the development.

[12] The method of producing a relief pattern of a cured film according to
[11], wherein the step of coating the resin composition on a substrate and drying the resin composition to form the resin film comprises a step of coating the resin composition on a substrate using a slit nozzle.

[13] An organic EL display device, wherein the cured film according to [9] or [10] which is patterned or not patterned is arranged in one or both of a planarizing layer and a dielectric layer of a first electrode of a driving circuit.

[14] An electronic component or a semiconductor apparatus, wherein the cured film according to [9] or [10] patterned or not pattered is arranged between rewires as an interlayer dielectric film.

[15] The electronic component or a semiconductor apparatus according to [14], wherein the rewires are copper metal wires, and the width of the copper metal wires and the distance between adjacent wires are 5 μm or less.

[16] An electronic component or a semiconductor apparatus, wherein the cured film according to [9] or [10] patterned or not patterned is arranged between rewires as an interlayer dielectric film on an encapsulation resin substrate on which a silicon chip has been arranged.

[17] The semiconductor electronic component or the semiconductor apparatus according to any one of [14] to [16], wherein the rewires are copper metal wires and are connected with a semiconductor chip via a bump.

[18] The semiconductor electronic component or the semiconductor apparatus according to any one of [14] to [17], wherein, for the rewires, the width of metal wires and the distance between adjacent wires get thinner as the wires get closer to the semiconductor chip.

[19] The semiconductor electronic component or the semiconductor apparatus according to any one of [14] to [18], wherein the thickness of the interlayer dielectric film arranged between the rewires gets thinner as the interlayer dielectric film gets closer to the semiconductor chip.

[20] A method of producing an electronic component or a semiconductor apparatus, comprising steps of arranging the cured film according to [9] or [10] on a support substrate on which a temporary attachment material has been arranged as an interlayer dielectric film between rewires, arranging a silicon chip and an encapsulation resin thereon, and detaching the support substrate on which the temporary attachment material has been arranged and the rewires.

Effect of the Invention

Provided is a resin composition capable of providing a cured film which is excellent in chemical resistance and film properties even by a thermal treatment at a low temperature of 200° C. or less, a heat-resistant resin used in the resin composition, and further a di-amine compound which is a raw material thereof.

MODE FOR CARRYING OUT THE INVENTION

Figure 1:
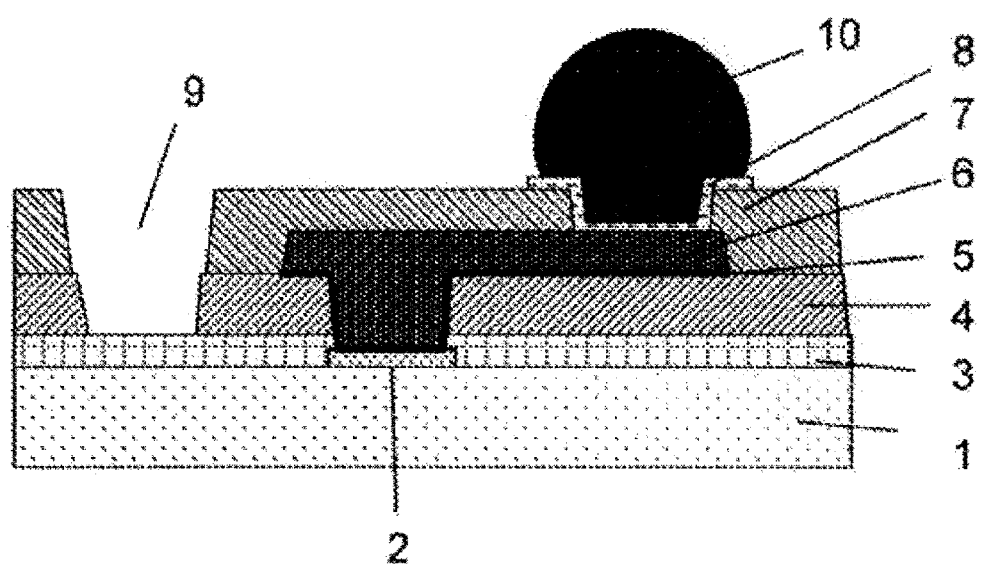
FIG. 1 is a schematic diagram illustrating an enlarged cross section of a pad portion of a semiconductor apparatus having a bump.

The present invention will be described in detail below.
<A Di-Amine Compound Represented by the General Formula (1)>

The present invention is a di-amine compound represented by the above general formula (1). In the di-amine compound represented by the general formula (1), $R^1$ and $R^2$ each are a divalent aliphatic group.

$R^3$ and $R^4$ are each a divalent aliphatic group, aliphatic ring group, aromatic group, a divalent organic group in which an aromatic group is bonded by —O—, —CO—, —SO$_2$—, —CH$_2$—, —C(CH$_3$)$_2$— or —C(CF$_3$)$_2$— (wherein F is fluorine), a divalent organic group in which two or more aromatic groups are bonded by a single bond, or a divalent organic group in which two or more aromatic groups are bonded by —O—, —CO—, —SO$_2$—, —CH$_2$—, —C(CH$_3$)$_2$— or —C(CF$_3$)$_2$— (wherein F is fluorine).

$R^5$ and $R^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group. Among them, $R^5$ and $R^6$ each are preferably a hydrogen atom or an aliphatic group because dehydration and ring closure at a low temperature is facilitated.

A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine).

When R$^3$ to R$^6$ and A each are an organic group having an aromatic group, they contain a hydroxyl group and a part or all of the hydrogen on the aromatic ring may be substituted with a hydroxyl group. p and q each are independently an integer number in the range of 0 to 3.

It should be noted that the present invention does not exclude the case in which R$^1$ and R$^3$ or R$^2$ and R$^4$ are groups of the same kind. That is, in such a case, it is understood that a group of the kind having the smallest number of carbon atoms (for example, a methylene group in the case of an aliphatic group) and a group excluding that group exist (for example, when a propylene group is present in a portion corresponding to —R$^3$—R$^1$—, a combination of a methylene group and an ethylene group is interpreted).

[Chem 8]

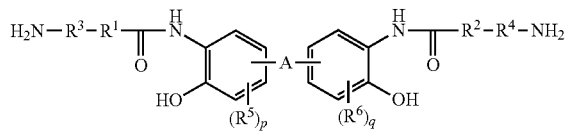

(1)

When R$^1$ and R$^2$ have an aliphatic group, the di-amine compound itself can undergo dehydration and ring closure at 200° C. or lower and thus have an oxazole portion. As a result, high chemical resistance can be obtained even by curing at a low temperature, and due to the flexibility of the aliphatic group, a cured film with a high degree of elongation can be obtained.

It is preferred that R$^1$ and R$^2$ in the general formula (1) each are independently a divalent aliphatic group represented by the general formula (2) or the general formula (3). The divalent aliphatic group represented by the general formula (2) or the general formula (3) is preferred because the divalent aliphatic group has high flexibility, resulting in a greater effect of improving the degree of elongation.

[Chem 9]

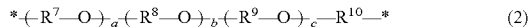

$$*\!-\!(\!-\!R^7\!-\!O\!-\!)_a\!-\!(\!-\!R^8\!-\!O\!-\!)_b\!-\!(\!-\!R^9\!-\!O\!-\!)_c\!-\!R^{10}\!-\!* \quad (2)$$

In the general formula (2), R$^7$ to R$^{10}$ each are independently a C$_1$-C$_{10}$ alkylene group, and each of a, b and c is an integer number in the range of 1≤a≤20, 0≤b≤20, and 0≤c≤20, and the arrangement of the repeating units may be in a block way or in a random way. * indicates a chemical bond (in other words, an end portion of a divalent group). From the viewpoint of the influence on the heat resistance, the temperature of dehydration and ring closure and the degree of elongation, 1≤a+b+c≤10 is preferable.

[Chem 10]

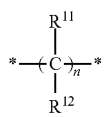

(3)

In the general formula (3), R$^{11}$ and R$^{12}$ each are independently hydrogen, fluorine, or a C$_1$-C$_6$ alkyl group, and n is an integer number of 1 to 20. * indicates a chemical bond (in other words, an end portion of a divalent group).

In terms of flexibility, R$^{11}$ and R$^{12}$ each are preferably hydrogen or a C$_1$-C$_2$ alkyl group.

n is preferably 3 or more in terms of stretchability and is preferably 10 or less in terms of heat resistance of the obtained compound.

R$^3$ represented by the general formula (1) and in the general formula (1) is a divalent organic group represented by the formula (4) and R$^4$ in the general formula (1) is preferably a divalent organic group represented by the formula (5).

[Chem 11]

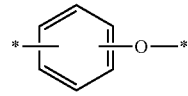

(4)

(In the general formula (4), * indicates a chemical bond (in other words, an end portion of a divalent group.)

[Chem 12]

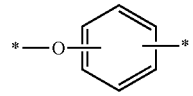

(5)

(In the general formula (5), * indicates a chemical bond (in other words, an end portion of a divalent group).)

The oxygen in the formula (4) is preferably bonded to the R$^1$ side and the oxygen in the formula (5) is preferably bonded to the R$^2$ side.

The phenoxy group represented by the formula (4) or the formula (5) is preferably bonded directly to the amino group and an aliphatic group because the solubility of the di-amine compound is suppressed, and high chemical resistance can be obtained. In addition, a phenyl group and an aliphatic group form an ether bond, which is preferable because stretchability and a high degree of elongation are obtained. Furthermore, a part or all of the hydrogen on the benzene ring may be substituted with an alkyl group preferably having 5 or less carbon atoms or a monovalent aromatic group having preferably 10 or less carbon atoms.

<A Method of Producing a Di-Amine Compound Represented by the General Formula (1)>

The di-amine compound represented by the general formula (1) can be produced according to a known method of producing a di-amine compound. The method is not particularly limited, but the following method can be applied.

As a first step, to a solution in which the hydroxy di-amine compound described below is dissolved, a phthalimide acid chloride derivative is added dropwise in the presence of a tertiary amine such as triethylamine, an epoxy compound such as propylene oxide, an unsaturated cyclic ether such as dihydropyran, an unsaturated bond-containing compound such as ethyl methacrylate. In order to facilitate the purification of the diphthalimide form after the reaction, a dehydrochlorination reaction is preferably carried out in the presence of an epoxy compound, an unsaturated cyclic ether compound and an unsaturated bond-containing compound. The dehydrochlorination reaction is particularly preferably carried out in the presence of an epoxy compound, an unsaturated cyclic ether compound.

In the second step, the phthalic acid is eliminated from the diphthalimide form, whereby obtaining a di-amine represented by the above general formula (1). As a method of eliminating phthalic acid, hydrazine, methylhydrazine, or the like can be used. As a solvent, alcohol can be used. This deprotection step can be carried out by heating under reflux.

[Chem 13]

(The first step)

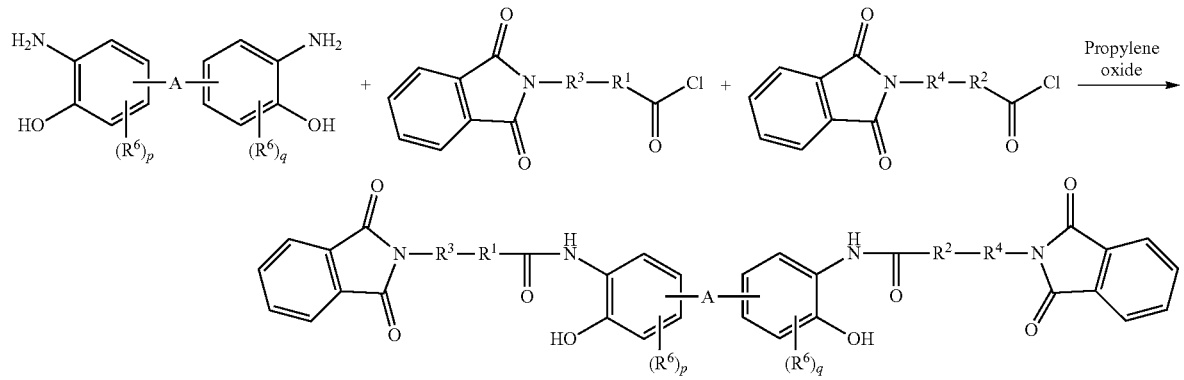

(The second step)

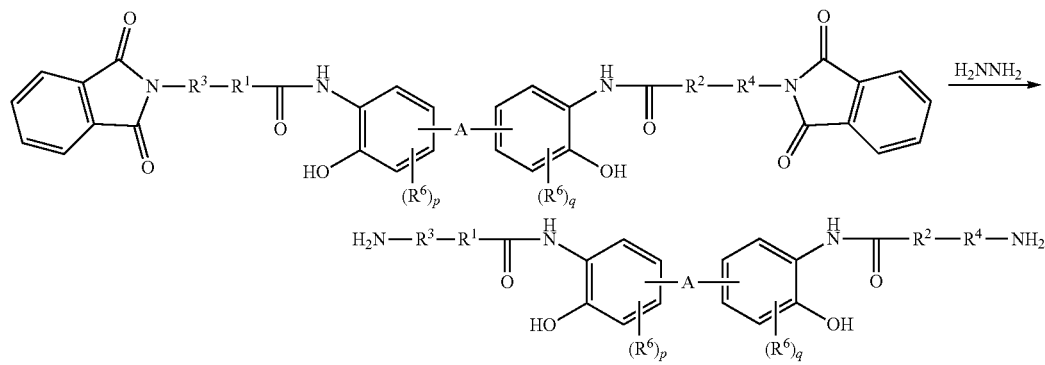

($R^1$ and $R^2$ each are a divalent aliphatic group.

$R^3$ and $R^4$ are each a divalent aliphatic group, aliphatic ring group, aromatic group, a divalent organic group in which an aromatic group is bonded by —O—, —CO—, —$SO_2$—, —$CH_2$—, —$C(CH_3)_2$— or $C(CF_3)_2$— (wherein F is fluorine), a divalent organic group in which two or more aromatic groups are bonded by a single bond, or a divalent organic group in which two or more aromatic groups are bonded by —O—, —CO—, —$SO_2$—, —$CH_2$—, —$C(CH_3)_2$— or —$C(CF_3)_2$— (wherein F is fluorine).

$R^5$ and $R^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group.

A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —$SO_2$—, —$CH_2$—, —$C(CH_3)_2$— or —$C(CF_3)_2$— (wherein F is fluorine).

p and q each are independently an integer number in the range of 0 to 3).

When $R^3$ is a divalent organic group represented by the formula (4) and $R^4$ in the general formula (1) is represented by the formula (5), the production by the following method is preferred.

As a first step, to a solution in which the hydroxy di-amine compound described below is dissolved, a nitrocarboxylic acid chloride derivative is added dropwise in the presence of a tertiary amine such as triethylamine, an epoxy compound such as propylene oxide, an unsaturated cyclic ether such as dihydropyran, an unsaturated bond-containing compound such as ethyl methacrylate. In order to facilitate the purification of the dinitro form after the reaction, a dehydrochlorination reaction is preferably carried out in the presence of an epoxy compound, an unsaturated cyclic ether compound and an unsaturated bond-containing compound. The dehydrochlorination reaction is particularly preferably carried out in the presence of an epoxy compound, an unsaturated cyclic ether compound.

In the second step, the dinitro form is reduced, and thus a di-amine represented by the above general formula (1) can be obtained. Examples of the reduction method to be used include a method of reacting a hydrogen gas in the presence of a metal catalyst such as palladium/carbon and Raney nickel, a method of reacting ammonium formate in the presence of a metal catalyst such as palladium/carbon and Raney nickel, a method of using tin(I) chloride and hydrochloric acid, a method of using iron and hydrochloric acid, a method of using hydrazine, and the like.

[Chem 14]

(The first step)

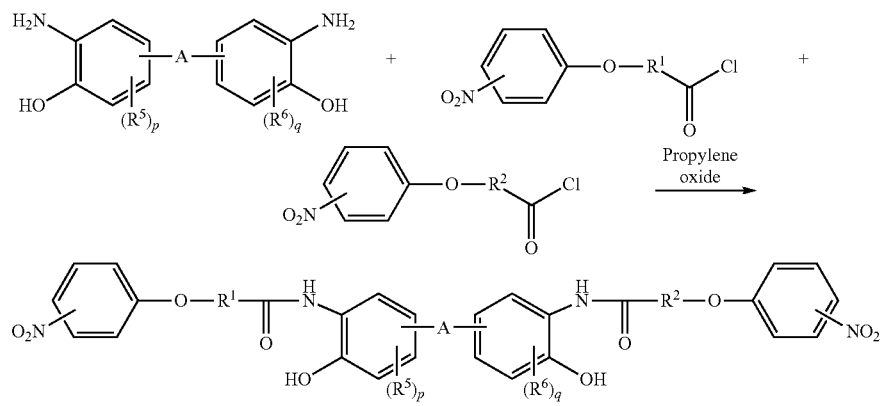

(The second step)

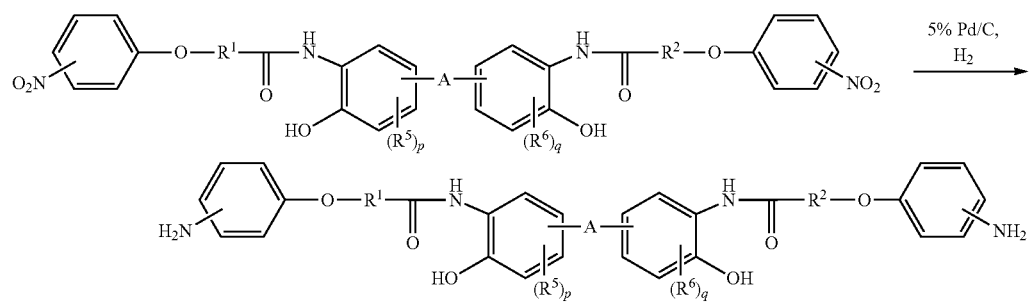

(In the general formula (1), $R^1$ and $R^2$ each are a divalent aliphatic group.

$R^5$ and $R^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group.

A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine).

p and q each are an integer number in the range of 0 to 3).

Examples of reaction solvents include ketones such as methyl isobutyl ketone, diisobutyl ketone, cyclohexanone, methyl ethyl ketone, acetone and the like, esters such as ethyl acetate, butyl acetate, isobutyl acetate and the like, ethers such as tetrahydrofuran, dimethoxyethane, diethoxyethane, dibutyl ether, diethylene glycol dimethyl ether and the like. Among them, from the viewpoint of solubility and versatility, acetone is more preferably used. One of these can be used alone, or two kinds or more can be used in combination. The amount of the reaction solvent to be used is preferably in the range of 100 to 5000 parts by mass with respect to 100 parts by mass of the di-amine compound from the viewpoint of solubility.

Examples of the di-amine compound include hydroxyl group-containing di-amines such as bis(3-amino-4-hydroxyphenyl)hexafluoropropane (BAHF), bis(3-amino-4-hydroxyphenyl) sulfone, bis(3-amino-4-hydroxyphenyl)propane, bis(3-amino-4-hydroxyphenyl)methylene, bis(3-amino-4-hydroxyphenyl)ether, bis(3-amino-4-hydroxy)biphenyl, bis(3-amino-4-hydroxyphenyl)fluorene and the like, carboxyl group-containing di-amines such as 3,5-diaminobenzoic acid, 3-carboxy-4,4'-diaminodiphenyl ether and the like, sulfonic acid-containing di-amines such as 3-sulfonic acid-4,4'-diaminodiphenyl ether and the like, dithiohydroxyphenylenedi-amine and the like.

<Heat-Resistant Resin Used in the Present Invention>

The heat-resistant resin of the present invention is a heat-resistant resin having a structure derived from the di-amine compound described by the general formula [1], and may also be a precursor of a heat-resistant resin.

As described later, the heat-resistant resin of the present invention may contain a di-amine residue other than the di-amine residue derived from the general formula (1). The ratio of the di-amine residues derived from the general formula (1) to the total di-amine residues is desirably 50% by mole or more and 100% by mole or less. The content ratio is preferably greater than or equal to such a lower limit value because a cured film which is excellent in chemical resistance and film properties can be obtained even by a thermal treatment at a low temperature.

At least one of a polyimide, a polyamide, a polybenzoxazole, a polybenzimidazole, a polybenzothiazole, a precursor thereof, and a copolymer thereof, which are contained in the heat-resistant resin of the present invention, preferably have a structure derived from the di-amine compound of the present invention.

In the heat-resistant resin of the present invention, the polyamide preferably has a structure represented by the general formula (6), the polyimide precursor and the polyimide preferably have one or more kind of structures selected from the structures represented by the general formulas (7) and (8), and the polybenzoxazole preferably has a structure represented by the general formula (9).

[Chem 15]

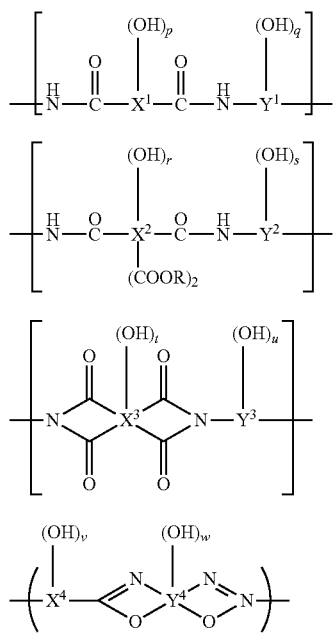

(In the general formulas (6) to (9), $Y^1$ to $Y^4$ each are an organic group derived from the general formula (1), $Y^1$ to $Y^3$ each are independently a tetravalent to hexavalent organic group, and $Y^4$ is a hexavalent to octavalent organic group. $X^1$ is a divalent to hexavalent organic group, $X^2$ and $X^3$ each are independently a tetravalent to decavalent organic group, and $X^4$ is a divalent to hexavalent organic group. R is a hydrogen atom or a $C_1$-$C_{20}$ organic group. q, s, u and w each are independently an integer of 2 to 4, and p, r, t and v each are independently an integer of 0 to 4.)

In the above general formula (6), $X^1$ and $X^4$ each are a divalent to hexavalent organic group having 2 or more carbon atoms and represent a structural component of an acid. $X^1$ and $X^4$ each are an aromatic dicarboxylic acids such as terephthalic acid, isophthalic acid, diphenylether dicarboxylic acid, naphthalene dicarboxylic acid, bis(carboxyphenyl)propane or the like, an aliphatic dicarboxylic acid such as cyclobutane dicarboxylic acid, cyclohexane dicarboxylic acid, malonic acid, dimethylmalonic acid, ethylmalonic acid, isopropylmalonic acid, di-n-butylmalonic acid, succinic acid, tetrafluorosuccinic acid, methylsuccinic acid, 2,2-dimethylsuccinic acid, 2,3-dimethylsuccinic acid, dimethylmethylsuccinic acid, glutaric acid, hexafluoroglutaric acid, 2-methylglutaric acid, 3-methylglutaric acid, 2,2-dimethylglutaric acid, 3,3-dimethylglutaric acid, 3-ethyl-3-methylglutaric acid, adipic acid, octafluoro adipate, 3-methyl adipate, octafluoro adipate, pimelic acid, 2,2,6,6-tetramethylpimelic acid, suberic acid, dodecafluorosuberic acid, azelaic acid, sebacic acid, hexadecafluorosebacic acid, 1,9-nonanedioic acid, dodecanedioic acid, tridecanedioic acid, tetradecanedioic acid, pentadecanedioic acid, hexadecanedioic acid, heptadecanedioic acid, octadecanedioic acid, nonadecanedioic acid, eicosanedioic acid, heneicosanedioic acid, docosanedioic acid, tricosanedioic acid, tetracosanedioic acid, pentacosanedioic acid, hexacosanedioic acid, heptacosanedioic acid, octacosanedioic acid, nanocosanedioic acid, triacontanedioic acid, hentriacontanedioic acid, dotriacontanedioic acid, diglycolic acid and the like, a dicarboxylic acid represented by the following general formula, a tricarboxylic such as trimellitic acid, trimesic acid and the like, those obtained by substituting a part of hydrogen atoms of these aromatic rings or hydrocarbons with a $C_1$-$C_{10}$ alkyl group, a fluoroalkyl group, a halogen atom or the like, a structure derived from those containing a bond such as —S—, —SO—, —SO$_2$—, —NH—, —NCH$_2$—, —N(CH$_2$CH$_3$)—, —N(CH$_2$CH$_2$CH$_3$)—, —N(CH(CH$_3$)$_2$)—, —COO—, —CONH—, —OCONH—, or —NHCONH—, and the like.

[Chem 16]

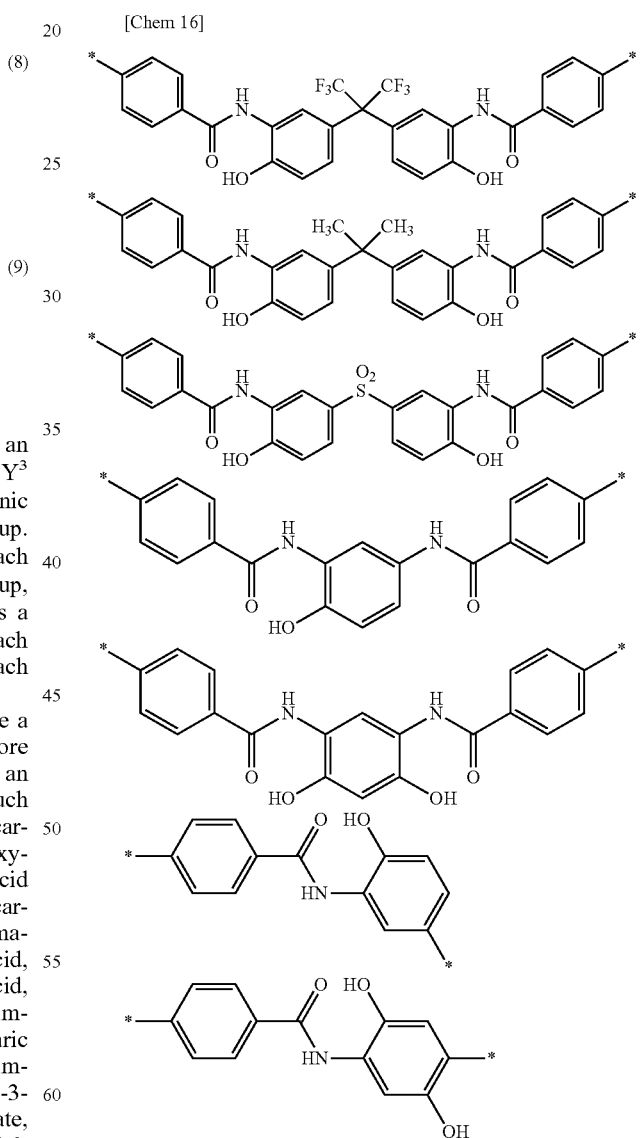

(The asterisk represents the binding site of a carboxyl group.)

Among them, $X^1$ and $X^4$ each are preferably a structure derived from a dicarboxylic acid having an aromatic group because a ring closure is unlikely to occur at the time of thermal curing, and thus, it is possible to suppress the increase in stress due to shrinkage of the film and improve the adhesion property.

For the production of the heat-resistant resin of the present invention, when polycondensation is carried out, for example, a compound in which a carboxylic acid group of a raw material compound of $X^1$ and $X^4$ is modified with a group which activates the reactivity of a carboxylic acid group as shown in the following general formula is used.

[Chem 17]

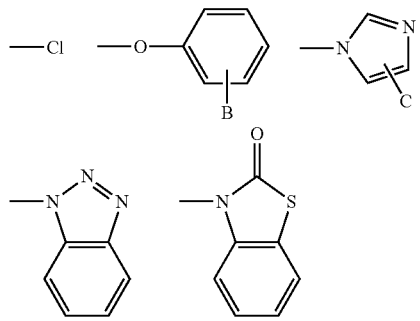

In the formula, B and C each are independently, but not limited to, a hydrogen atom, a methyl group, an ethyl group, a propyl group, an isopropyl group, a t-butyl group, a trifluoromethyl group, a halogen group, a phenoxy group, a nitro group and the like.

Among them, an active group other than a chloride compound is preferably used. By using an active group other than a chloride compound, chlorine ions in the resulting resin can be reduced, and the detachment from a metal substrate due to the presence of chlorine ions can be prevented. Further, as the active group, a diimidazolide compound is preferably used. Since the leaving group of the diimidazolide compound becomes a water-soluble imidazole, the reprecipitation and washing of the resulting resin can be carried out with water. Furthermore, since the imidazole that has left is basic, the imidazole acts as a ring closure accelerator of the polyimide precursor structure during polymerization. Thus, it is possible to increase the ratio of the cyclization for imidization at the stage of the polyamide resin production. As a result, the ratio of the cyclization when a cured film is produced by a thermal treatment can be lowered.

$Y^1$ to $Y^3$ in the general formulas (6) to (8) each are a tetravalent to hexavalent organic group, and $Y^4$ is a hexavalent to octavalent organic group and represents an organic group derived from a di-amine.

Since the heat-resistant resin has a structure derived from the di-amine compound represented by the general formula (1), $Y^1$ to $Y^4$ in the general formulas (6) to (8) contain a phenolic hydroxyl group. When a di-amine residue having a phenolic hydroxyl group is contained, an appropriate solubility of the resin in an alkali developing solution can be obtained. Therefore, a high contrast of the exposed part and unexposed part can be obtained, and a desired pattern can be formed.

The heat-resistant resin used in the present invention may have a structure derived from a di-amine compound having a phenolic hydroxyl group other than the di-amine compound represented by the general formula (1).

Specific examples thereof include, but are not limited to, aromatic di-amines such as bis(3-amino-4-hydroxyphenyl) hexafluoropropane, bis(3-amino-4-hydroxyphenyl) sulfone, bis(3-amino-4-hydroxyphenyl)propane, bis(3-amino-4-hydroxyphenyl)methylene, bis(3-amino-4-hydroxyphenyl) ether, bis(3-amino-4-hydroxy)biphenyl, 2,2'-ditrifluoromethyl-5,5'-dihydroxyl-4,4'-diaminobiphenyl, bis(3-amino-4-hydroxyphenyl)fluorene, 2,2'-bis(trifluoromethyl)-5,5'-dihydroxybenzidine and the like, compounds obtained by substituting a part of hydrogen atoms of these aromatic rings and hydrocarbons with a $C_1$-$C_{10}$ alkyl group, a fluoroalkyl group, a halogen atom or the like, or di-amines having a structure shown below, and the like. Other di-amines to be copolymerized can be used directly or as corresponding diisocyanate compounds or trimethylsilylated di-amines. Two kinds or more of these di-amine components may be used in combination.

[Chem 18]

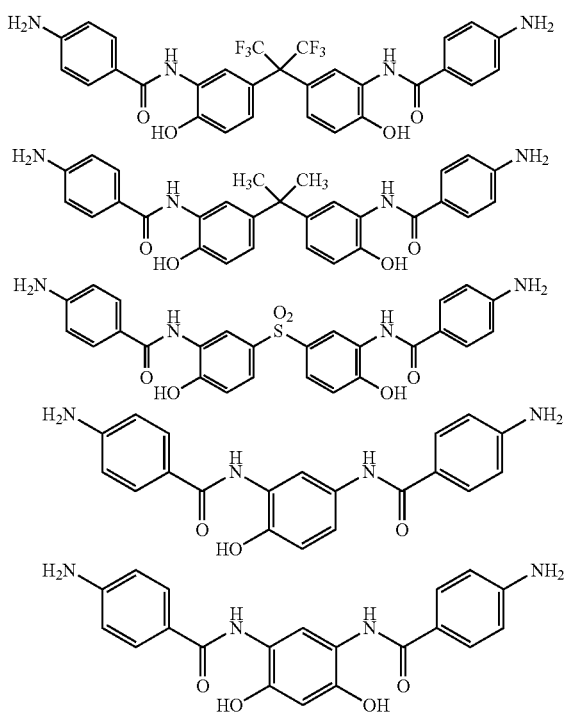

[Chem 19]

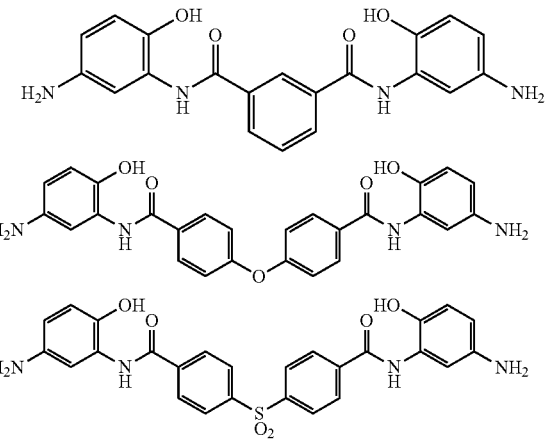

-continued

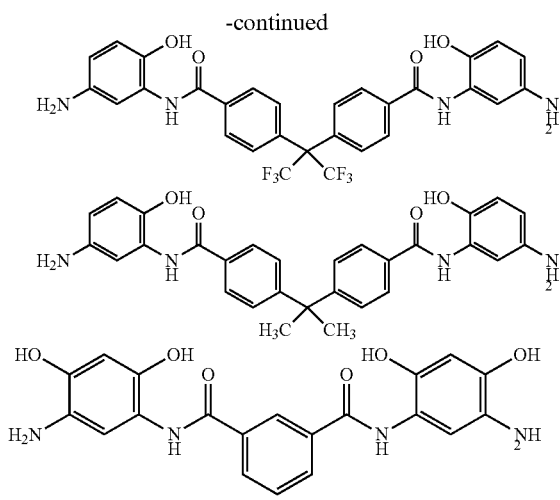

The heat-resistant resin of the present invention may contain a residue of a di-amine different than a di-amine having a phenolic hydroxyl group. Copolymerization thereof can improve the heat resistance.

Specific examples of the di-amine residue having an aromatic group include, but not limited to, aromatic di-amines such as 3,4'-diaminodiphenyl ether, 4,4'-diaminodiphenyl ether, 3,4'-diaminodiphenylmethane, 4,4'-diaminodiphenylmethane, 3,4'-diaminodiphenylsulfone, 4,4'-diaminodiphenylsulfone, 3,4'-diaminodiphenylsulfide, 4,4'-diaminodiphenylsulfide, 1,4-bis(4-aminophenoxy)benzene, benzine, m-phenylenedi-amine, p-phenylenedi-amine, 1,5-naphthalenedi-amine, 2,6-naphthalenedi-amine, bis(4-aminophenoxyphenyl)sulfone, bis(3-aminophenoxyphenyl) sulfone, bis(4-aminophenoxy)biphenyl, bis{4-(4-aminophenoxy)phenyl}ether, 1,4-bis(4-aminophenoxy) benzene, 2,2'-dimethyl-4,4'-diaminobiphenyl, 2,2'-diethyl-4,4'-diaminobiphenyl, 3,3'-dimethyl-4,4'-diaminobiphenyl, 3,3'-diethyl-4,4'-diaminobiphenyl, 2,2',3,3'-tetramethyl-4,4'-diaminobiphenyl, 3,3',4,4'-tetramethyl-4,4'-diaminobiphenyl, 2,2'-bis(trifluoromethyl)-4,4'-diaminobiphenyl and the like, compounds obtained by substituting a part of hydrogen atoms of these aromatic rings and hydrocarbons with a $C_1$-$C_{10}$ alkyl group, a fluoroalkyl group, a halogen atom or the like, and the like. Other di-amines to be copolymerized can be used directly or as corresponding diisocyanate compounds or trimethylsilylated di-amines. Two kinds or more of these di-amine components may be used in combination.

Further, the heat-resistant resin of the present invention preferably contains a di-amine residue having an aliphatic group in addition to a residue derived from the di-amine compound represented by the general formula (1). A di-amine residue having an aliphatic group has high affinity for a metal, so a resin having a high adhesion property with metal can be obtained. Since the aliphatic di-amine is highly basic and acts as a ring closure accelerator during polymerization, it is possible to increase the ratio of the cyclization of the imide skeleton at the stage of the polyamide resin production. As a result, the ratio of the cyclization at the time of thermal curing can be lowered, and the contraction of the cured film and the resulting increase in stress of the cured film can be suppressed. From this, it is possible to suppress the decrease in adhesion due to stress. Furthermore, since the flexible aliphatic di-amine residue contributes to a higher degree of elongation of the polyamide, a cured film having a better adhesion property with the metal, a low stress property and a high degree of elongation can be obtained.

The aliphatic group-containing di-amine used in the heat-resistant resin of the present invention preferably has at least one organic group of an alkylene group and an alkyl ether group. Specific examples thereof include di-amines selected from at least one of alkylene groups, cycloalkyl groups, alkylether groups, and cycloalkylether groups. A part of hydrogen atoms of these hydrocarbons may be substituted with a $C_1$-$C_{10}$ alkyl group, fluoroalkyl group, a halogen atom or the like, and a bond such as —S—, —SO—, —SO$_2$—, —NH—, —NCH$_3$—, —N(CH$_2$CH$_3$)—, —N(CH$_2$CH$_2$CH$_3$)—, —N(CH(CH$_3$)$_2$)—, —COO—, —CONH—, —OCONH—, —NHCONH— or the like may be contained, and these organic groups may have an unsaturated bond or an aliphatic ring structure.

Specific compound examples of di-amines having an aliphatic group include ethylenedi-amine, 1,3-diaminopropane, 2-methyl-1,3-propanedi-amine, 1,4-diaminobutane, 1,5-diaminopentane, 2-methyl-1,5-diaminopentane, 1,6-diaminohexane, 1,7-diaminoheptane, 1,8-diaminooctane, 1,9-diaminononane, 1,10-diaminodecane, 1,11-diaminoundecane, 1,12-diaminododecane, 1,2-cyclohexanedi-amine, 1,3-cyclohexanedi-amine, 1,4-cyclohexanedi-amine, 1,2-bis(aminomethyl)cyclohexane, 1,3-bis(aminomethyl)cyclohexane, 1,4-bis(aminomethyl)cyclohexane, 4,4'-methylenebis(cyclohexylamine), 4,4'-methylenebis(2-methyl cyclohexylamine), 1,2-bis(2-aminoethoxy)ethane, KH-511, ED-600, ED-900, ED-2003, EDR-148, EDR-176, D-200, D-400, D-2000, THF-100, THF-140, THF-170, RE-600, RE-900, RE-2000, RP-405, RP-409, RP-2005, RP-2009, RT-1000, HE-1000, HT-1100, HT-1700 (the above are trade names, manufactured by Huntsman Corporation), and the following compounds in which a part of hydrogen atoms of these aromatic rings or hydrocarbons may be substituted with a $C_1$-$C_{10}$ alkyl group, fluoroalkyl group, a halogen atom or the like, and which may contain a bond such as —S—, —SO—, —SO$_2$—, —NH—, —NCH$_3$—, —N(CH$_2$CH$_3$)—, —N(CH$_2$CH$_2$CH$_3$)—, —N(CH(CH$_3$)$_2$)—, —COO—, —CONH—, —OCONH—, —NHCONH— or the like.

[Chem 20]

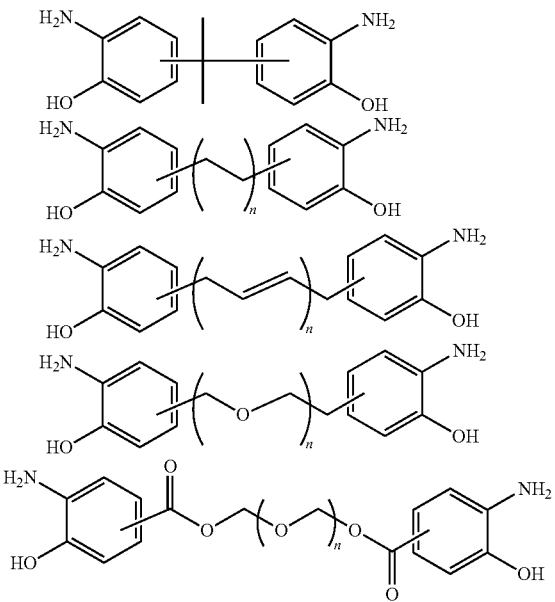

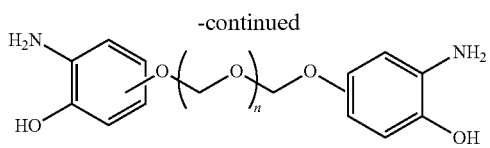

(n is independently an integer number of 1 to 10, preferably 1 to 5).

In the present invention, the di-amine having an aliphatic group is an organic group having at least one selected from alkylene groups and alkylether groups, and those having a non-cyclic structure in which the main chain is linear are preferred because flexibility and stretchability are obtained, and lower stress and a higher degree of elongation can be achieved when a cured film is formed.

Among alkyl ethers, a tetramethylene ether group is preferred because it is excellent in heat resistance and can impart a metal adhesion property after the evaluation of reliability. Examples thereof include, but are not limited to, RT-1000, HE-1000, HT-1100, HT-1700, (the above are trade names, manufactured by Huntsman Corporation)

By using such a di-amine having an aliphatic group, the solubility in an alkali solution can be maintained while a low stress property, high degree of elongation, and a high metal adhesion property can be achieved in the obtained cured film.

In the present invention, the content of the di-amine residues having an aliphatic group is preferably 5 to 40% by mole in the total di-amine residues. It is preferred that the content is 5% by mole or more because an effect of high metal adhesion by the di-amine residues having an aliphatic group can be obtained, and that the content is 40% by mole or less because the moisture absorption property of the resin decreases, and the detachment from the metal substrate can be prevented, resulting in a cured film with a high reliability.

The arrangement of the repeating units of the di-amine residues having an aliphatic group may be in a block way or in a random way, but preferably contained in a polyamide structure because a high metal adhesion property and lower stress can be imparted to the polyamide structure, and additionally, the degree of elongation improves.

Furthermore, in order to improve the adhesion property to a silicon substrate, in the heat-resistant resin of the present invention, an aliphatic group having a siloxane structure may be copolymerized. Specific examples thereof include those in which, as a di-amine component, bis(3-aminopropyl)tetramethyldisiloxane, bis(p-amino-phenyl)octamethylpentasiloxane or the like is copolymerized by 1 to 10% by mole.

In the above general formula (7) which is a polyimide precursor structure and the general formula (8) which is a polyimide structure, $X^1$ and $X^3$ each represent a residue of an acid dianhydride, and a tetravalent to decavalent organic group.

Specific examples of the acid dianhydride include, but are not limited to, aromatic tetracarboxylic dianhydrides pyromellitic dianhydride, 3,3',4,4'-biphenyl tetracarboxylic dianhydride, 2,3,3',4'-biphenyl tetracarboxylic dianhydride, 2,2',3,3'-biphenyl tetracarboxylic dianhydride, 3,3',4,4'-benzophenonetetracarboxylic dianhydride, 2,2',3,3'-benzophenone tetracarboxylic dianhydride, 2,2-bis(3,4-dicarboxyphenyl)propane dianhydride, 2,2-bis(2,3-dicarboxyphenyl)propane dianhydride, 1,1-bis(3,4-dicarboxyphenyl)ethane dianhydride, 1,1-bis(2,3-dicarboxyphenyl)ethane dianhydride, bis(3,4-dicarboxyphenyl)methane dianhydride, bis(2,3-dicarboxyphenyl)methane dianhydride, bis(3,4-dicarboxyphenyl)sulfone dianhydride, bis(3,4-dicarboxyphenyl)ether dianhydride, 1,2,5,6-naphthalene tetracarboxylic dianhydride, 9,9-bis(3,4-dicarboxyphenyl)fluorenic dianhydride, 9,9-bis{4-(3,4-dicarboxyphenoxy)phenyl}fluorenic dianhydride, 2,3,6,7-naphthalene tetracarboxylic dianhydride, 2,3,5,6-pyridine tetracarboxylic dianhydride, 3,4,9,10-perylene tetracarboxylic dianhydride, 2,2-bis(3,4-dicarboxyphenyl)hexafluoropropane dianhydride, 3,3',4,4'-diphenylsulfone tetracarboxylic dianhydride, 1,2,3,4-cyclobutane tetracarboxylic dianhydride, 1,2,3,4-cyclopentane tetracarboxylic dianhydride, 1,2,4,5-cyclohexane tetracarboxylic dianhydride, 3,4-dicarboxy-1,2,3,4-tetrahydro-1-naphthalenesuccinic dianhydride, 5-(2,5-dioxotetrahydrofuryl)-3-methyl-3-cyclohexene-1,2-dicarboxylic dianhydride, 2,3,5-tricarboxy-2-cyclopentaneacetic dianhydride, bicyclo[2.2.2]oct-7-ene-2,3,5,6-tetracarboxylic dianhydride, 2,3,4,5-tetrahydrofuran tetracarboxylic dianhydride, 3,5,6-tricarboxy-2-norbornaneacetic dianhydride, 1,3,3a,4,5,9b-hexahydro-5(tetrahydro-2,5-dioxo-3-furanyl)naphtho[1,2-c] furan-1,3-dione and an acid dianhydride having the structure shown in the following formula, compounds obtained by substituting a part of hydrogen atoms of these aromatic rings and hydrocarbons with a $C_1$-$C_{10}$ alkyl group, a fluoroalkyl group, a halogen atom or the like.

[Chem 21]

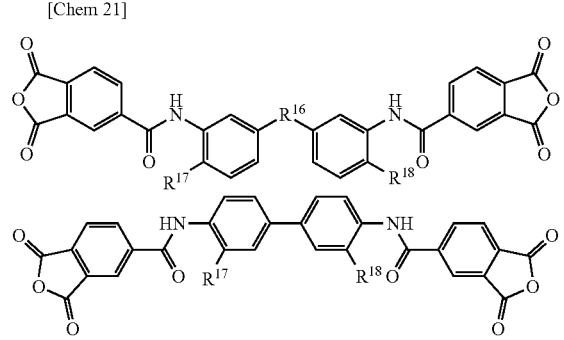

$R^{16}$ represents an oxygen atom, $C(CF_3)_2$, $C(CH_3)_2$ or $SO_2$, and $R^{17}$ and $R^{18}$ each represent a hydrogen atom, a hydroxyl group or a thiol group.

Among them, 3,3',4,4'-biphenyltetracarboxylic dianhydride, 2,3,3',4'-biphenyltetracarboxylic dianhydride, 2,2',3,3'-biphenyltetracarboxylic dianhydride, 3,3',4,4'-benzophenonetetracarboxylic dianhydride, 2,2',3,3'-benzophenonetetracarboxylic dianhydride, 2,2-bis(3,4-dicarboxyphenyl)propane dianhydride, 2,2-bis(2,3-dicarboxyphenyl)propane dianhydride, 1,1-bis(3,4-dicarboxyphenyl)ethane dianhydride, 1,1-bis(2,3-dicarboxyphenyl)ethane dianhydride, bis(3,4-dicarboxyphenyl)methane dianhydride, bis(2,3-dicarboxyphenyl)methane dianhydride, bis(3,4-dicarboxyphenyl)sulfone dianhydride, bis(3,4-dicarboxyphenyl)ether dianhydride, 2,2-bis (3,4-dicarboxyphenyl)hexafluoropropane dianhydride, 3,3',4,4'-diphenylsulfonetetracarboxylic dianhydride, 9,9-bis(3,4-dicarboxyphenyl)fluorenic dianhydride, 9,9-bis{4-(3,4-dicarboxyphenoxy)phenyl}fluorenic dianhydride, butanetetracarboxylic dianhydride, 1,2,3,4-cyclopentanetetracarboxylic dianhydride, 1,2,4,5-cyclohexanetetracarboxylic dianhydride, 1,3,3a,4,5,9b-hexahydro-5(tetrahydro-2,5-dioxo-3-furanyl)naphtho[1,2-c] furan-1,3-dione are preferred. One of these can be used alone, or two kinds or more can be used in combination.

R in the general formula (7) is a hydrogen atom or a $C_1$-$C_{20}$ monovalent organic group. From the viewpoint of the solubility in an alkali developing solution and the solution stability of the resulting photosensitive resin composition, 10% by mole to 90% by mole of R is preferably hydrogen. Further, R preferably contains at least one $C_1$-$C_{16}$ monovalent hydrocarbon group and the rest is preferably hydrogen atoms.

The mole ratio of the structures represented by the general formulas (6) to (9) in the present invention can be determined by a method of calculating the mole ratio from the mole ratio of the monomers used in the polymerization or by a method of detecting the peaks of the polyamide structure, the imide precursor structure and the imide structure in the resulting resin, the photosensitive resin composition, and the cured film by a nuclear magnetic resonance apparatus (NMR).

The heat-resistant resin of the present invention has preferably a weight average molecular weight in the range of 3,000 to 200,000. Within this range, an appropriate solubility of the resin in an alkali developing solution can be obtained. Therefore, a high contrast of the exposed part and unexposed part can be obtained, and a desired pattern can be formed. The heat-resistant resin of the present invention has more preferably a weight average molecular weight of 100,000 or less, and even more preferably 50,000 or less from the viewpoint of solubility in an alkali developing solution. The heat-resistant resin of the present invention preferably has a weight average molecular weight of 1.0000 or more in terms of the improvement in the degree of elongation. The molecular weight herein can be measured by gel permeation chromatography (GPC) and converted from a standard polystyrene calibration curve.

In order to improve the pot life of the resin composition of the present invention, ends of the main chain of the heat-resistant resin may be capped with another end cap compound such as a monoamine, a monocarboxylic acid, an anhydride, a mono-active ester compound or the like.

In order to suppress the decrease in solubility in an alkali solution due to an increased weight average molecular weight of the heat-resistant resin of the present invention, the introduction ratio of the end cap compound is preferably 0.1% by mole or more, more preferably 5% by mole or more with respect to the total amine component. In order to suppress the decrease in mechanic properties of the resulting cured film due to a decreased weight average molecular weight of the polyamide resin, the introduction ratio of the end cap compound is preferably 60% by mole or less, and more preferably 50% by mole or less. A plurality of different end groups may be introduced by reacting several end cap compounds.

Specific examples of a monoamine as an end cap compound include M-600, M-1000, M-2005, M-2070 (the above are trade names, manufactured by Huntsman Corporation), aniline, 2-ethynylaniline, 3-ethynylaniline, 4-ethynylaniline, 5-amino-8-hydroxyquinoline, 1-hydroxy-7-aminonaphthalene, 1-hydroxy-6-aminonaphthalene, 1-hydroxy-5-aminonaphthalene, 1-hydroxy-4-aminonaphthalene, 2-hydroxy-7-aminonaphthalene, 2-hydroxy-6-aminonaphthalene, 2-hydroxy-5-aminonaphthalene, 1-carboxy-7-aminonaphthalene, 1-carboxy-6-aminonaphthalene, 1-carboxy-5-aminonaphthalene, 2-carboxy-7-aminonaphthalene, 2-carboxy-6-aminonaphthalene, 2-carboxy-5-aminonaphthalene, 2-aminobenzoic acid, 3-aminobenzoic acid, 4-aminobenzoic acid, 4-aminosalicylic acid, 5-aminosalicylic acid, 6-aminosalicylic acid, 2-aminobenzenesulfonic acid, 3-aminobenzenesulfonic acid, 4-aminobenzenesulfonic acid, 3-amino-4,6-dihydroxypyrimidine, 2-aminophenol, 3-aminophenol, 4-aminophenol, 2-aminothiophenol, 3-aminothiophenol, 4-aminothiophenol and the like. Two kinds or more of these can be used.

For the monocarboxylic acid and the mono-active ester compound as an end cap compound, monocarboxylic acids such as 3-carboxyphenol, 4-carboxyphenol, 3-carboxythiophenol, 4-carboxythiophenol, 1-hydroxy-7-carboxynaphthalene, 1-hydroxy-6-carboxynaphthalene, 1-hydroxy-5-carboxynaphthalene, 1-mercapto-7-carboxynaphthalene, 1-mercapto-6-carboxynaphthalene, 1-mercapto-5-carboxynaphthalene, 3-carboxybenzenesulfonic acid, 4-carboxybenzenesulfonic acid and the like, active ester compounds in which these carboxyl groups are esterified, acid anhydrides such as phthalic anhydride, maleic anhydride, nadic anhydride, cyclohexanedicarboxylic anhydride, 3-hydroxyphthalic anhydride and the like, dicarboxylic acids such as phthalic acid, maleic acid, maleic acid, nadic acid, cyclohexanedicarboxylic acid, 3-hydroxy phthalic acid, 5-norbornene-2,3-dicarboxylic acid, tricarboxylic acids such as trimellitic acid, trimesic acid, diphenyl ether tricarboxylic acid, active ester compounds obtained by the reaction of one carboxyl group of dicarboxylic acids such as terephthalic acid, phthalic acid, maleic acid, cyclohexanedicarboxylic acid, 1,5-dicarboxynaphthalene, 1,6-dicarboxynaphthalene, 1,7-dicarboxynaphthalene, 2,6-dicarboxynaphthalene with N-hydroxybenzotriazole, imidazole, N-hydroxy-5-norbornene-2,3-dicarboximide, compounds obtained by substituting a part of hydrogen atoms of these aromatic rings and hydrocarbons with a $C_1$-$C_{10}$ alkyl group, a fluoroalkyl group, a halogen atom or the like can be used. Two kinds or more of these can be used.

The resin ends and the resin side chains of the heat-resistant resin in the present invention have preferably a structure sealed with an imide precursor such as an amide acid or amide acid ester or an imide. Since the resin ends have more sites in contact with other components and the substrate than the main chain of the resin, the adhesion property can be enhanced, and the pot life of the resin composition can be improved. Therefore, an imide precursor structure or an imide precursor structure is preferably contained, and the polyimide precursor structure represented by the general formula (7) and the polyimide structure represented by the general formula (8) are more preferably present near the end of the heat-resistant resin. Thus, the adhesion property can be enhanced, and the pot life of the alkali-soluble resin can be further enhanced. For this purpose, the polyamide structure is, after the copolymerization, preferably copolymerized with at least one structure of the polyimide precursor structure and the polyimide structure.

The structure of the heat-resistant resin of the present invention in which a resin end or a resin side chain is capped with an imide precursor such as an amide acid or amide acid ester or an imide can be obtained from, but not limited to, acid anhydrides such as phthalic anhydride, maleic anhydride, nadic anhydride, cyclohexanedicarboxylic anhydride, 3-hydroxyphthalic anhydride and the like, dicarboxylic acids such as phthalic acid, maleic acid, maleic acid, nadic acid, cyclohexanedicarboxylic acid, 3-hydroxy phthalic acid, 5-norbornene-2,3-dicarboxylic acid, tricarboxylic acids such as trimellitic acid, trimesic acid, diphenyl ether tricarboxylic acid, active ester compounds obtained by the reaction of one carboxyl group of dicarboxylic acids such as terephthalic acid, phthalic acid, maleic acid, cyclohexanedicarboxylic acid, 1,5-dicarboxynaphthalene, 1,6-dicarboxynaphthalene, 1,7-dicarboxynaphthalene, 2,6-dicarboxynaphthalene with N-hydroxybenzotriazole, imidazole, N-hydroxy-5-norbornene-2,3-dicarboximide, compounds obtained by substituting a part of hydrogen atoms of these aromatic rings and hydrocarbons with a $C_1$-$C_{10}$ alkyl group, a fluoroalkyl group, a halogen atom or the like.

The end cap compound which can be used in the present invention can be detected easily according to the following methods. For example, the alkali-soluble resin in which an end cap compound has been introduced is dissolved in an acidic solution to decompose the resin into structural units of the amine component and the acid anhydride component, which can be subjected to gas chromatography (GC) or NMR. Thus, the end cap compound used in the present invention can be easily detected. In a different way, the detection is also easily possible by measuring directly the alkali-soluble resin component in which an end cap compound has been introduced by pyrolysis gas chromatography (PGC), infrared spectrum and $^{13}$C-NMR spectrum.

The heat-resistant resin of the present invention is synthesized by the following method, for example, but the method is not limited thereto.

First, a compound in which a dicarboxylic acid is substituted with an active carboxylic acid group, or an acid dianhydride, a di-amine compound represented by the general formula (1), and other copolymerization components are dissolved in an organic solvent at room temperature, optionally at an elevated temperature, and the mixture is then heated for polymerization. From the viewpoint of the stability of the solution at the time of the reaction, the di-amine compound having a high solubility is preferably dissolved first. Thereafter, in some cases, other copolymerization components are added, and an acid or an acid anhydride which will act as an end cap compound is added for polymerization.

When a di-amine having an aliphatic group different than the di-amine compound represented by the general formula (1) is introduced, the reaction is preferably carried out at 70 to 200° C.

The polyimide precursor structure is a structure derived from an acid anhydride in the above polymerization method, and in the case of an amide acid ester, can be obtained by reacting a carboxylic acid with an esterifying agent after the polymerization.

The heat-resistant resin of the present invention includes a case of a polyimide, and the polyimide can be synthesized by, for example, after an imide precursor is obtained using a method of producing a structure represented by the general formula (7), a method of polymerizing the imide precursor at 70° C. to 200° C., a method of closing all the imide rings of the imide precursor using a known imidization reaction method, a method of stopping the imidization reaction in the middle and thus partially introducing an imide structure, or a method of partially introducing an imide structure by mixing a ring-closed imide polymer in which all the imide rings of the imide precursor are closed with the polyimide precursor.

The benzoxazole used in the present invention can be synthesized, for example, after a polyamide is obtained, by polymerizing the polyamide at 150 to 250° C., or a method of ring-closing the polyamide by adding an acidic catalyst. Examples of the organic solvent used for polymerization of the resin include, but are not limited to, amides such as N,N-dimethylformamide, N,N-dimethylacetamide, N-methyl-2-pyrrolidone, 1,3-dimethyl-2-imidazolidinone, N,N'-dimethylpropylene urea, N,N-dimethylisobutyramide, methoxy-N,N-dimethylpropionamide, cyclic esters such as γ-butyrolactone, γ-valerolactone, δ-valerolactone, γ-caprolactone, ε-caprolactone, α-methyl-γ-butyrolactone, carbonates such as ethylene carbonate and propylene carbonate, glycols such as triethylene glycol, phenols such as m-cresol and p-cresol, acetophenone, 1,3-dimethyl-2-imidazolidinone, sulfolane, dimethyl sulfoxide, tetrahydrofuran, dimethyl sulfoxide, propylene glycol monomethyl ether acetate, ethyl lactate and the like.

After the polymerization by the above method, the heat-resistant resin of the present invention is preferably introduced in a large amount of water or a mixture of methanol and water, precipitated, filtered off, dried, and isolated. The drying temperature is preferably 40 to 100° C., more preferably 50 to 80° C. By this operation, unreacted monomers and oligomer components of dimers, trimers and the like are removed, and the film properties after thermal curing can be improved.

The imidization ratio of the heat-resistant resin of the present invention can be easily obtained by the following method, for example. First, the infrared absorption spectrum of the polymer is measured, and the presence of an absorption peak of an imide structure derived from the polyimide is confirmed (near 1780 cm$^{-1}$, 1377 cm$^{-1}$). Then, the infrared absorption spectrum of the polymer thermally treated at 350° C. for 1 hour, which is considered as a sample of 100% of the imidization ratio, is measured and the peak intensities near 1377 cm' of the resin are compared between before and after the thermal treatment to calculate the content of imide groups in the resin before the thermal treatment and thus determine the imidization ratio. Since the change in the ratio of cyclization upon the thermal curing is suppressed and the effect of reducing the stress can be obtained, the imidization ratio is preferably 50% or more, and more preferably 80% or more.

The heat-resistant resin obtained by the method of the present invention can be used as a resin composition. The heat-resistant resin obtained by the method of the present invention, (b) the resin composition in which a photo acid generator is used as a photosensitive compound can be used as a positive-type photosensitive resin composition (positive-type photosensitive varnish).

The resin obtained by the method of the present invention, the resin composition in which a photopolymerizable compound is used as a photosensitizing agent can be used as a negative-type photosensitive resin composition (negative-type photosensitive varnish).

Since the positive-type photosensitive composition is superior in resolution to the negative-type photosensitive resin composition, the positive-type photosensitive composition is suitable for the application of forming a fine processing pattern.

As the photo acid generator of the positive-type photosensitive resin composition, a quinonediazide compound is preferably used.

Examples of quinonediazide compounds include polyhydroxy compounds to which quinonediazide sulfonic acid is bound by ester, polyamino compounds to which quinonediazide sulfonic acid is bound by sulfonamide, polyhydroxy polyamino compounds to which quinonediazide sulfonic acid is bound by ester and/or sulfonamide and the like. All the functional groups of these polyhydroxy compounds, polyamino compounds and polyhydroxy polyamino compounds do not have to be substituted with quinonediazide, but on average, 40% by mole or more of the total functional groups is preferably substituted with quinonediazide. The use of such a quinonediazide compound can result in a positive-type photosensitive resin composition which is sensitive to common ultraviolet rays including the i-line (wavelength of 365 nm), h-line (wavelength of 405 nm) or g-line (wavelength of 436 nm) of a mercury lamp.

Specific examples of the polyhydroxy compounds include, but are not limited to, Bis-Z, BisP-EZ, TekP-4HBPA, TrisP-HAP, TrisP-PA, TrisP-SA, TrisOCR-PA, BisOCHP-Z, BisP-MZ, BisP-PZ, BisP-IPZ, BisOCP-IPZ, BisP-CP, BisRS-2P, BisRS-3P, BisP-OCHP, methylene tris-FR-CR, BisRS-26X, DML-MBPC, DML-MBOC, DML-OCHP, DML-PCHP, DML-PC, DML-PTBP, DML-34X, DML-EP, DML-POP, dimethylol-BisOC-P, DML-PFP, DML-PSBP, DML-MTrisPC, TriML-P, TriML-35XL, TML-BP, TML-HQ, TML-pp-BPF, TML-BPA, TMOM-BP, HML-TPPHBA, HML-TPHAP (the above are trade names, manufactured by Honshu Chemical Industry Co., Ltd.), BIR-OC, BIP-PC, BIR-PC, BIR-PTBP, BIR-PCHP, BIP-BIOC-F, 4PC, BIR-BIPC-F, TEP-BIP-A, 46DMOC, 46DMOEP, TM-BIP-A(the above are trade names, manufactured by ASAHI YUKIZAI CORPORATION), 2,6-dimethoxymethyl-4-t-butylphenol, 2,6-dimethoxymethyl-p-cresol, 2,6-diacetoxymethyl-p-cresol, naphthol, tetrahydroxybenzophenone, esters of methyl gallate, bisphenol A, bisphenol E, methylene bisphenol, BisP-AP(trade names, manufactured by Honshu Chemical Industry Co., Ltd.), novolac resins, and the like.

Specific examples of the polyamino compounds include, but are not limited to, 1,4-phenylenedi-amine, 1,3-phenylenedi-amine, 4,4'-diaminodiphenyl ether, 4,4'-diaminodiphenylmethane, 4,4'-diaminodiphenylsulfone, 4,4'-diaminodiphenyl sulfide, and the like.

Specific examples of the polyhydroxy polyamino compounds include, but are not limited to, 2,2-bis(3-amino-4-hydroxyphenyl)hexafluoropropane, 3,3'-dihydroxybenzidine and the like.

Among them, the quinonediazide compounds preferably contain esters of a phenol compound and a 4-naphthoquinonediazide sulfonyl group. In this case, a high sensitivity to the i-line exposure and higher resolution can be obtained.

The content of the quinonediazide compound used in the photosensitive resin composition of the present invention is preferably from 1 to 50 parts by mass, and more preferably from 10 to 40 parts by mass, with respect to 100 parts by mass of the resin. The content of the quinonediazide compound in this range is preferred because a higher sensitivity can be achieved due to the resulting contrast between the exposed portion and the unexposed portion, and residues which occur when the content is large are not observed. A sensitizer or the like may be added as necessary.

When the resin composition of the present invention contains a compound represented by the following general formula (10), the elongation property of the cured film after the reliability evaluation and the adhesion property to a metal material can be improved.

[Chem 22]

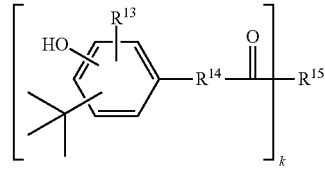

(10)

The compound represented by the general formula (10) acts as an antioxidant and suppresses the oxidative deterioration of the aliphatic groups and the phenolic hydroxyl groups of the heat-resistant resin. In addition, metal oxidation can be suppressed by the effect of rust prevention on the metal material.

In the general formula (10), $R^{13}$ is a hydrogen atom or an alkyl group having 2 or more carbon atoms, and $R^{14}$ is an alkylene group having 2 or more carbon atoms. $R^{15}$ represents a monovalent to tetravalent organic group containing at least one of an alkylene group having 2 or more carbon atoms, an O atom, and an N atom. k represents an integer of 1 to 4, and preferably 2 to 4 since a simultaneous action on the heat-resistant resin and the metal material is possible. Examples of $R^{15}$ include alkyl groups, cycloalkyl groups, alkoxy groups, alkyl ether groups, alkylsilyl groups, alkoxysilyl groups, aryl groups, aryl ether groups, carboxyl groups, carbonyl groups, allyl groups, vinyl groups, heterocyclic groups, —O—, —NH—, —NHNH—, combinations thereof, and the like, and may further have a substituent. Among these, from the viewpoint of solubility in a developing solution and the adhesion property to metal, an alkyl ether, and —NH— are preferred, and from the viewpoint of interaction with a heat-resistant resin and adhesion property to metal by metal complex formation, —NH— is more preferred.

Examples of the compound represented by the following general formula (10) include the following compounds, but not limited to the following structures.

[Chem 23]

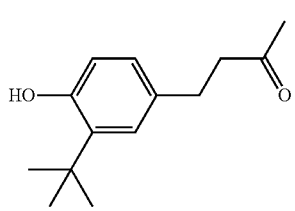 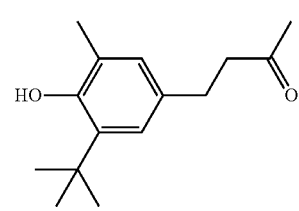 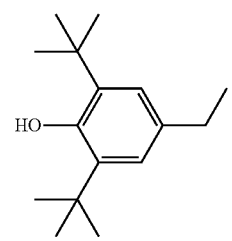

-continued
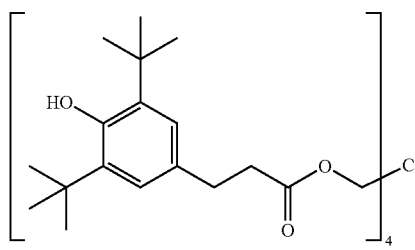
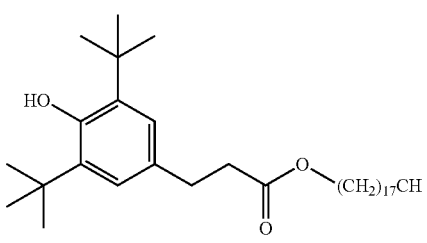
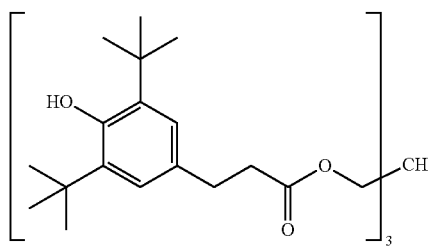
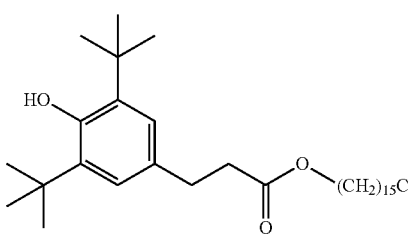
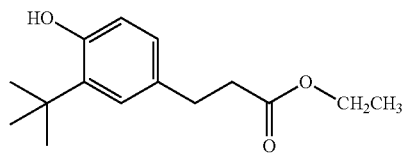
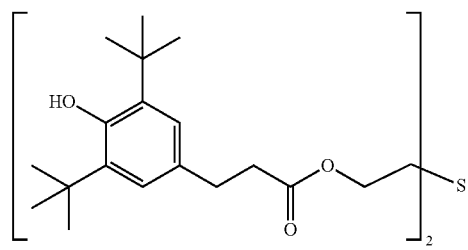
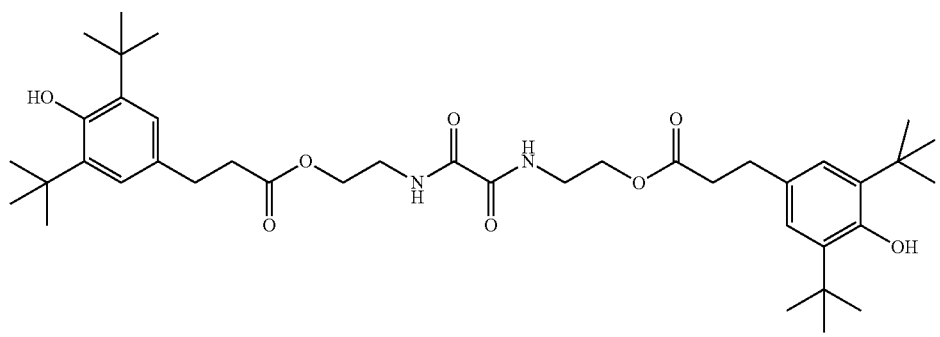
[Chem 24]
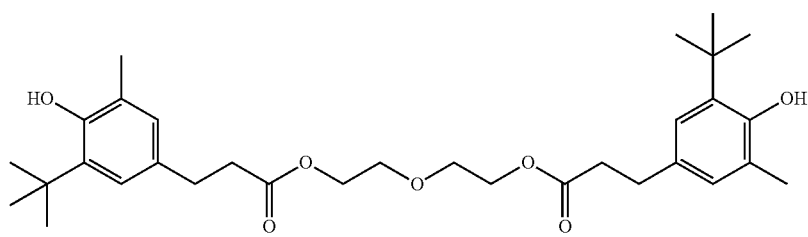
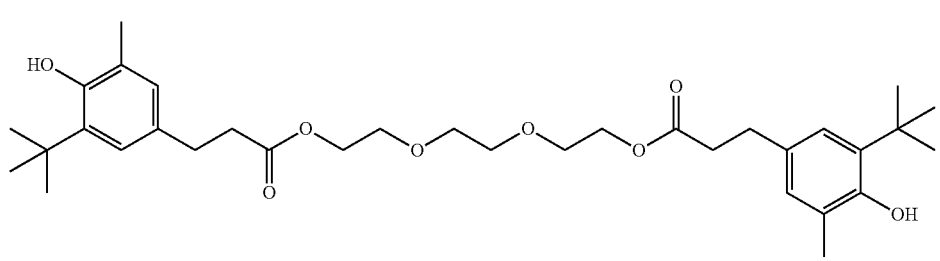

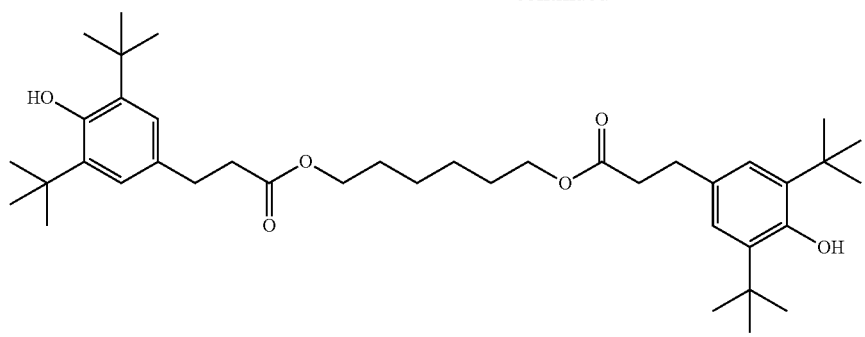
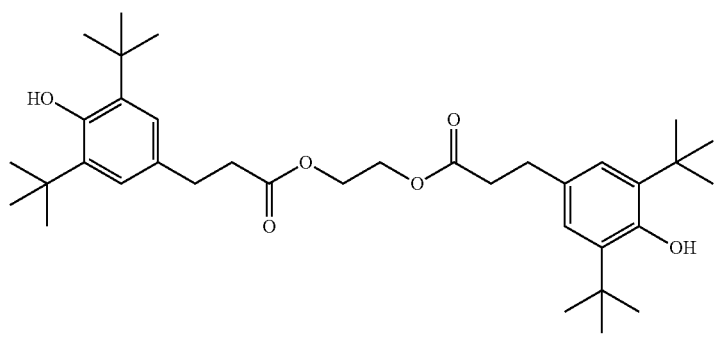
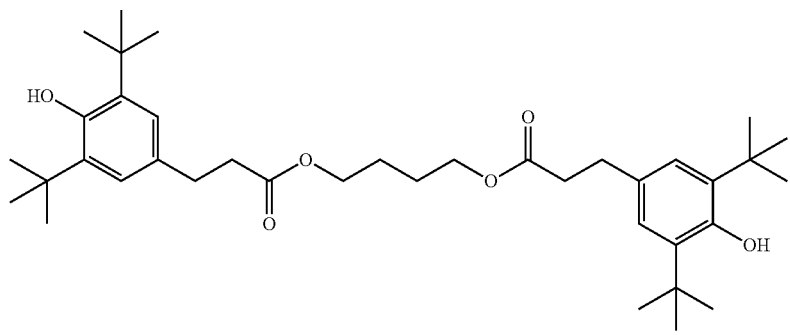
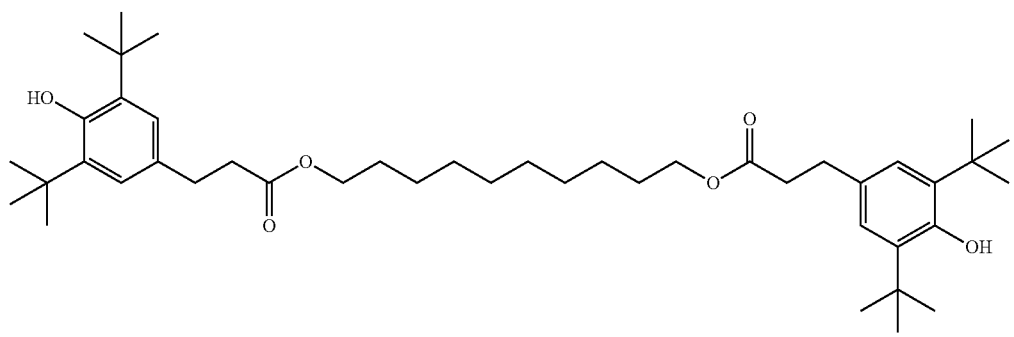
[Chem 25]
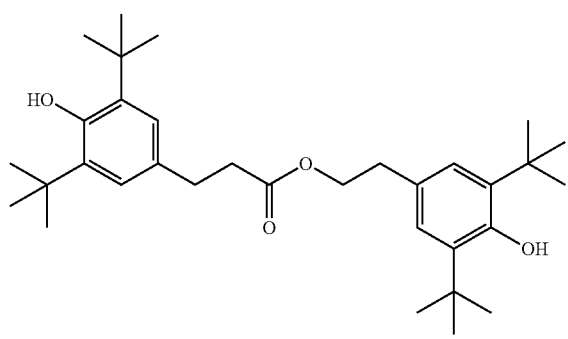

-continued
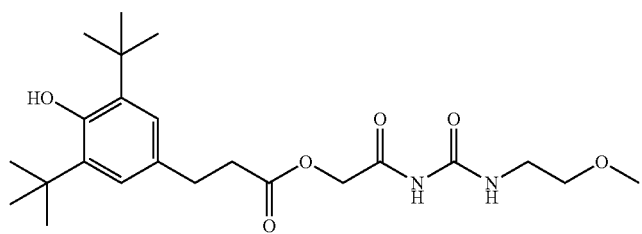
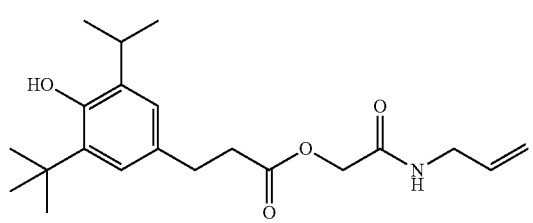
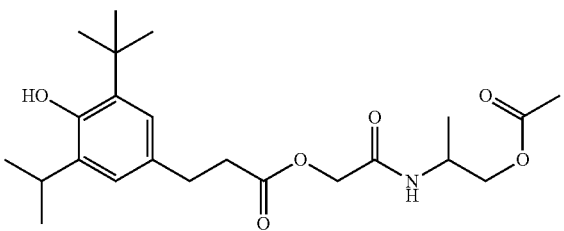
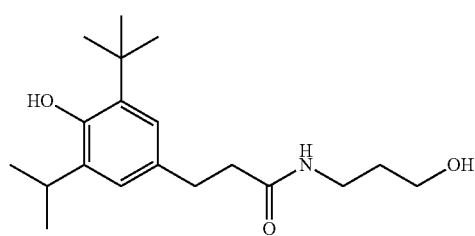
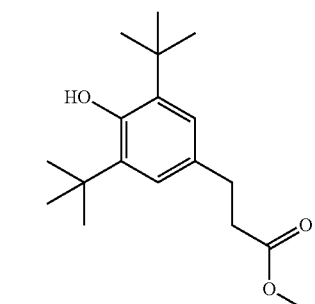
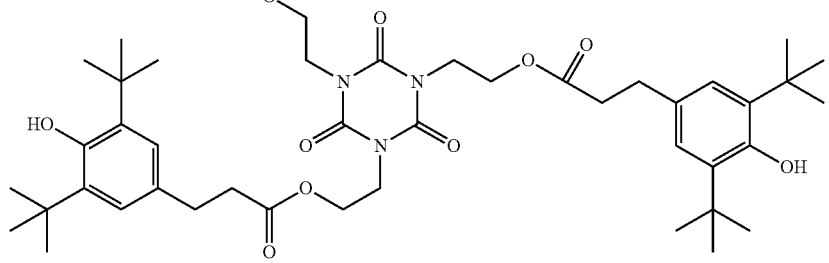
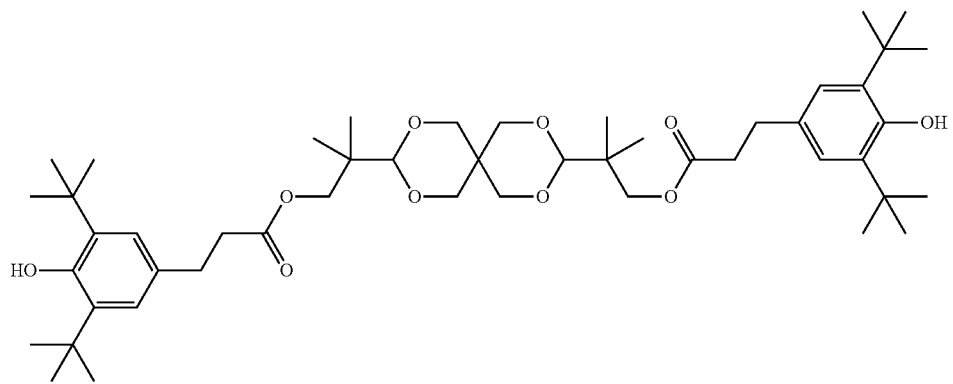

-continued
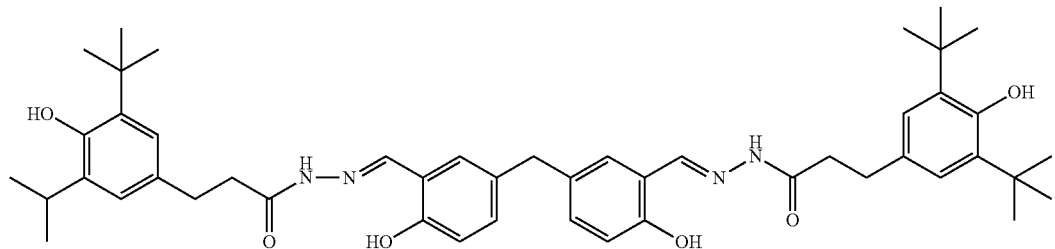
[Chem 26]
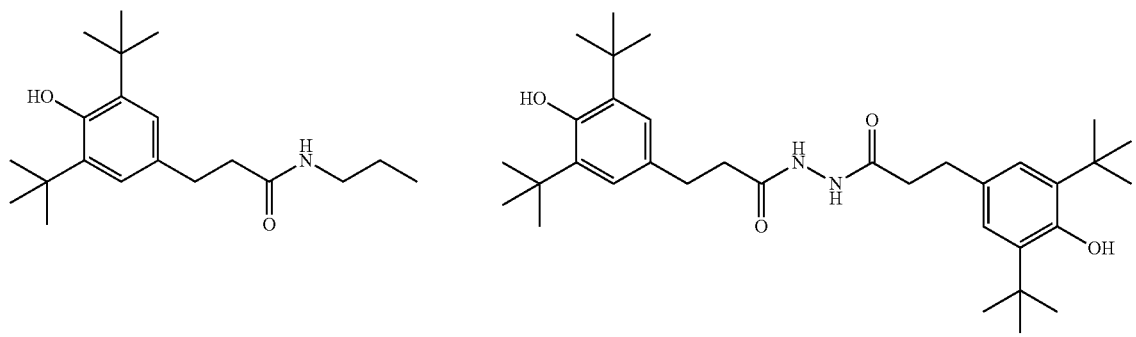
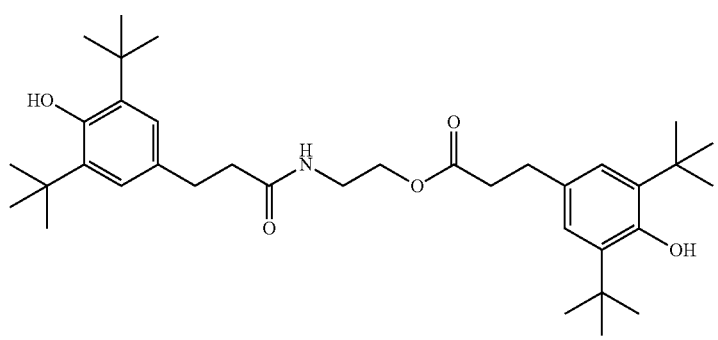
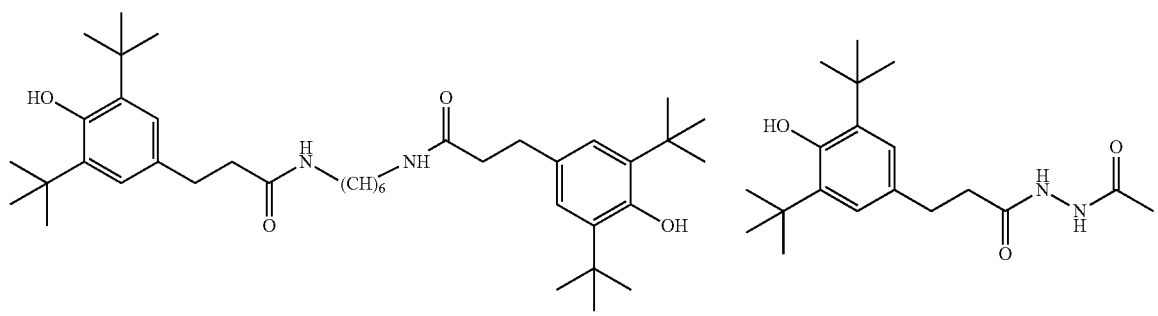
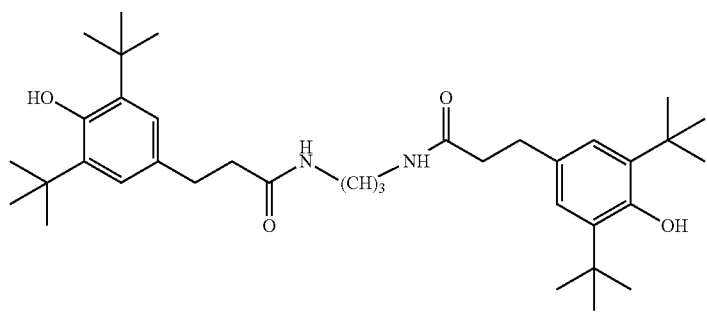

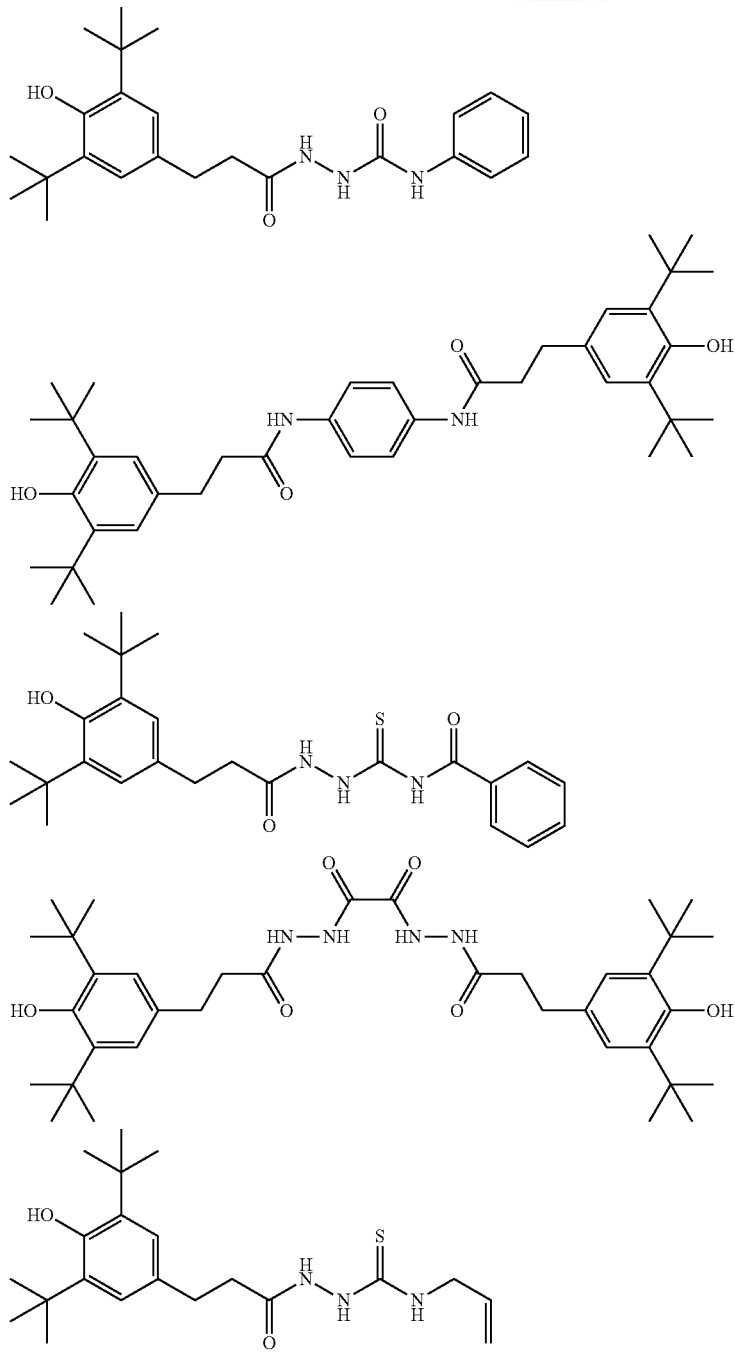

The amount to be added of the compound represented by the general formula (10) is preferably from 0.1 to 10 parts by mass, more preferably from 0.5 to 5 parts by mass, based on the heat-resistant resin. When the amount to be added is less than 0.1 parts by mass, it is difficult to obtain the elongation property after the reliability and the effect of improving the adhesion property to a metal material. When the amount to be added is more than 10 parts by mass, the sensitivity of the resin composition may be lowered due to the interaction with the photosensitizing agent.

The resin composition of the present invention preferably contains a thermal crosslinking agent. Specifically, a compound (d) having two or more of at least one of an alkoxymethyl group and a methylol group (hereinafter referred to as compound (d) in some cases) is preferred. The compound (d) may have two or more alkoxymethyl groups, or may have two or more methylol groups, or may contain one or more alkoxymethyl groups and one or more methylol groups. When two groups or more of these groups are contained, a rigid cross-linked structure can be obtained by the condensation reaction with the resin and similar molecules. The use in combination with a photo acid generator or a photopolymerization initiator can improve sensitivity as well as mechanical properties of the cured film, allowing for broader designs.

Preferred examples of these compounds include DML-PC, DML-PEP, DML-OC, DML-OEP, DML-34X, DML-PTBP, DML-PCHP, DML-OCHP, DML-PFP, DML-PSBP, DML-POP, DML-MBOC, DML-MBPC, DML-MTrisPC, DML-BisOC-Z, DMLBisOCHP-Z, DML-BPC, DML-BisOC-P, DMOM-PC, DMOM-PTBP, DMOM-MBPC, TriML-P, TriML-35XL, TML-HQ, TML-BP, TML-pp-BPF, TML-BPE, TML-BPA, TML-BPAF, TML-BPAP, TMOM-BP, TMOM-BPE, TMOM-BPA, TMOM-BPAF, TMOM-BPAP, HML-TPPHBA, HML-TPHAP, HMOM-TPPHBA, HMOM-TPHAP (the above are trade names, manufactured by Honshu Chemical Industry Co., Ltd.), and NIKALAC (registered trademark) MX-290, NIKALAC MX-280, NIKALAC MX-270, NIKALAC MX-279, NIKALAC MW-100LM, NIKALAC MX-750LM (the above are trade names, manufactured by SANWA CHEMICAL CO., LTD.). Two kinds or more of these can be contained. Among these, HMOM-TPHAP and MW-100LM are preferably added because the reflow is unlikely to occur during curing, and a pattern of a rectangle is obtained.

The amount to be added of the compound (d) having two or more of at least one of an alkoxymethyl group and a methylol group is preferably 10 to 60 parts by mass, more preferably 20 to 40 parts by mass, with respect to 100 parts by mass of the heat-resistant resin of the present invention. The amount to be added is preferably more than 10 parts by mass because the crosslinking density is high due to the thermal crosslinking agent, and thus the chemical resistance of the cured film is improved. The amount to be added is preferably less than 60 parts by mass because a sufficient flexibility and thus a high degree of elongation are obtained.

In addition, when the resin composition of the present invention contains a thermal crosslinking agent having a structural unit represented by the following general formula (11), an improved degree of elongation and a lower stress can be obtained.

[Chem 27]

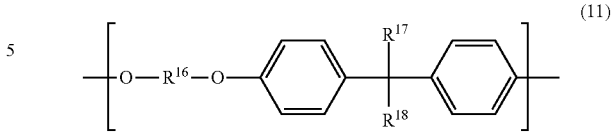

In the general formula (11), $R^{17}$ and $R^{18}$ each independently represents a hydrogen atom or a methyl group. $R^{16}$ is a divalent organic group having an alkylene group having 2 or more carbon atoms and may be either linear, branched or cyclic.

Examples of $R^{16}$ include alkylene groups, cycloalkylene groups, alkyl ether groups, alkylsilyl groups, alkoxysilyl groups, arylene groups, aryl ether groups, ester groups, carbonyl groups, heterocyclic groups, combinations thereof, and the like, and may further have a substituent.

Since the thermal crosslinking agent itself has a flexible alkylene group and a rigid aromatic group, it is possible to improve the degree of elongation and reduce stress while the heat resistance is maintained. Examples of crosslinking groups include, but are not limited to, acrylic groups, methylol groups, alkoxymethyl groups, epoxy groups. Among them, the epoxy groups are preferred because an epoxy group reacts with the phenolic hydroxyl group of the heat-resistant resin and can improve the heat resistance of the cured film and because a reaction without dehydration is possible.

Examples of the compound which contains a structural unit represented by the following general formula (11) include the following compounds, but not limited to the following structures.

[Chem 28]

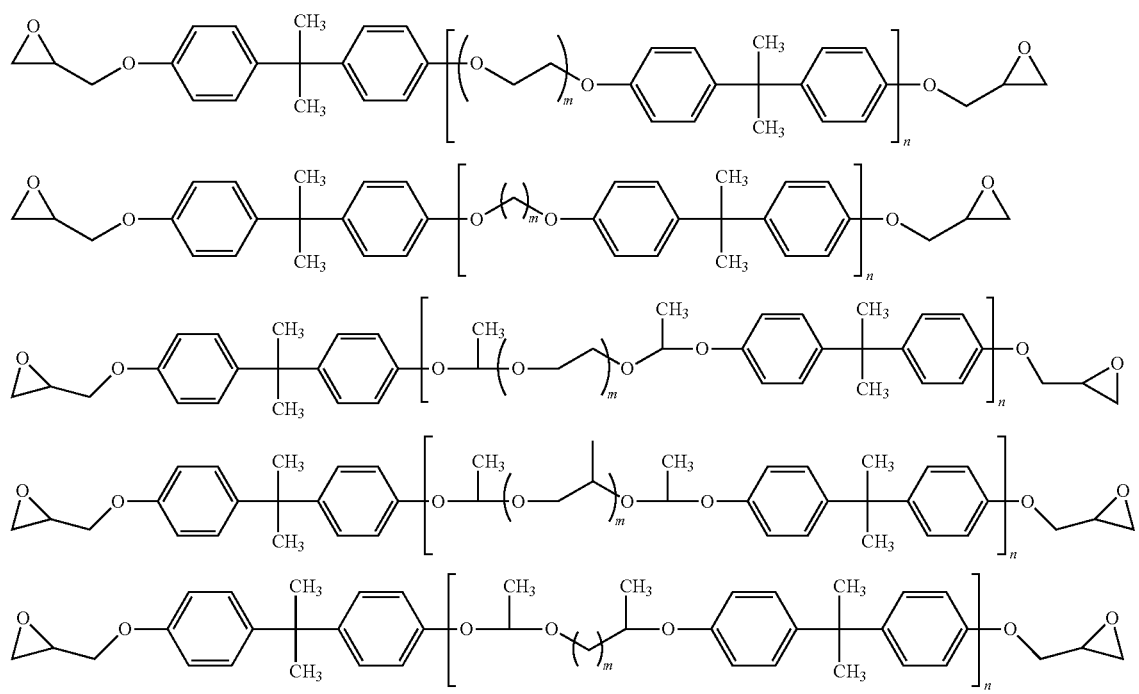

(In the formula, n is an integer of 1 to 5, and m is an integer of 1 to 20).

Among the above structures, n is preferably 1 to 2, and m is preferably 3 to 7 in order to achieve the heat resistance as well as the improved degree of elongation.

Furthermore, if necessary, a low molecular weight compound having a phenolic hydroxyl group may be contained as long as the shrinkage residual film rate after curing is not lowered. This way, the developing time can be shortened.

Examples of these compounds include Bis-Z, BisP-EZ, TekP-4HBPA, TrisP-HAP, TrisP-PA, BisOCHP-Z, BisP-MZ, BisP-PZ, BisP-IPZ, BisOCP-IPZ, BisP-CP, BisRS-2P, BisRS-3P, BisP-OCHP, methylenetris-FR-CR, BisRS-26X (the above are trade names, manufactured by Honshu Chemical Industry Co., Ltd.)), BIP-PC, BIR-PC, BIR-PTBP, BIR-BIPC-F (the above are trade names, manufactured by ASAHI YUKIZAI CORPORATION) and the like. Two kinds or more of these can be contained.

The content of the low molecular weight compound having a phenolic hydroxyl group is, with respect to 100 parts by mass of the heat-resistant resin, preferably 1 to 40 parts by mass.

The resin composition of the present invention preferably contains a solvent (c). Examples of solvents include polar aprotic solvents such as N-methyl-2-pyrrolidone, γ-butyrolactone, γ-valerolactone, δ-valerolactone, N,N-dimethylformamide, N,N-dimethylacetamide, dimethylsulfoxide, 1,3-dimethyl-2-imidazolidinone, N,N'-dimethylpropyleneurea, N,N-dimethylisobutyramide, and methoxy-N,N-dimethylpropionamide, ethers such as tetrahydrofuran, dioxane, propyleneglycolmonomethylethers, and propyleneglycolmonoethylether, ketones such as acetone, methylethylketone, and diisobutylketone, esters such as ethylacetate, butylacetate, isobutylacetate, propylacetate, propyleneglycolmonomethyletheracetate, and 3-methyl-3-methoxybutylacetate, ethyl lactate, methyl lactate, alcohols such as diacetone alcohol and 3-methyl-3-methoxybutanol, aromatic hydrocarbons such as toluene and xylene, and the like. Two kinds or more of these can be contained.

The content of the solvent is preferably 100 parts by mass or more with respect to 100 parts by mass or more of the heat-resistant resin in order to dissolve the composition, and 1,500 parts by mass or less in order to form a coating film having a film thickness of 1 μm.

In order to promote the wettability with the substrate, the resin composition of the present invention may also contain a surfactant, an ester such as ethyl lactate or propyleneglycol monomethylether acetate, an alcohol such as ethanol, a ketone such as cyclohexanone or methylisobutylketone, an ether such as tetrahydrofuran or dioxane.

In order to enhance the attachment with the substrate, within the range that does not impair the pot life, the resin composition of the present invention may contain, as a silicon component, a silane coupling agent such as trimethoxyaminopropylsilane, trimethoxyepoxysilane, trimethoxyvinylsilane, trimethoxythiol propylsilane or the like. With respect to 100 parts by mass of the heat-resistant resin, the preferred content of the silane coupling agent is preferably 0.01 to 5 parts by mass.

The resin composition of the present invention preferably contains another alkali-soluble resin in addition to the heat-resistant resin composition of the present invention. Specific examples thereof include siloxane resins, acrylic polymer obtained by copolymerization of acrylic acid, novolac resins, resole resins, polyhydroxystyrene resins, modified forms obtained by introducing into these a crosslink group such as a methylol group, an alkoxymethyl group, or an epoxy group, or copolymerized polymer thereof. Such resins are dissolved in an alkali solution of, such as, tetramethylammonium hydroxide, choline, triethylamine, dimethylaminopyridine, monoethanolamine, diethylaminoethanol, sodium hydroxide, potassium hydroxide, sodium carbonate or the like. When these alkali-soluble resins are contained, it is possible to impart the properties of each alkali-soluble resin while the adhesion property and the excellent sensitivity of the cured film are maintained.

Among them, phenolic resins such as novolac resins, resole resins, polyhydroxystyrene resins, and modified forms obtained by introducing to these a crosslink group such as a methylol group, an alkoxymethyl group or an epoxy group are preferred because, in addition to the improvement the sensitivity, a lower stress can be obtained since the shrinkage variation ratio before and after curing is low.

With respect to 100 parts by mass of the heat-resistant resin of the present invention, the preferred content of these resins is preferably 5 to 200 parts by mass, and more preferably 15 to 150 parts by mass.

Further, the resin composition of the present invention may contain a dissolution regulator within a range which does not increase the shrinkage ratio after curing. As the dissolution regulator, any compound which is generally used as a dissolution regulator in a positive resist can be preferably used. Examples thereof include polyhydroxy compounds, sulfonamide compounds, urea compounds, and the like. In particular, a polyhydroxy compound which is a raw material for the synthesis of a quinonediazide compound is preferably used.

When a photopolymerizable compound is blended, the resin composition of the present invention is a resin composition having a negative photosensitive property which indicates the insolubilization by light. The photopolymerizable compound contains a polymerizable unsaturated functional group. Examples of polymerizable unsaturated functional groups include unsaturated double bond functional groups such as vinyl groups, allyl groups, acryloyl groups, and methacryloyl groups and unsaturated triple bond functional groups such as propargyl. Among these, groups selected from vinyl groups, acryloyl groups and methacryloyl group of a conjugated system are preferred from the viewpoint of polymerization property.

The number of the functional groups contained is preferably 1 to 4 from the viewpoint of stability, and each group may not be necessarily the same. The photopolymerizable compound has preferably a number average molecular weight of 30 to 800. The number average molecular weight in the range of 30 to 800 results in a good compatibility with a polyamide and a good stability of the resin composition solution.

Preferred examples of photopolymerizable compounds include diethyleneglycoldiacrylate, triethyleneglycoldiacrylate, tetraethyleneglycoldiacrylate, diethyleneglycoldimethacrylate, triethyleneglycoldimethacrylate, tetraethyleneglycoldimethacrylate, trimethylolpropanediacrylate, trimethylolpropanetriacrylate, trimethylolpropanedimethacrylate, trimethylolpropanetrimethacrylate, styrene, α-methylstyrene, 1,2-dihydronaphthalene, 1,3-diisopropenylbenzene, 3-methylstyrene, 4-methylstyrene, 2-vinylnaphthalene, butylacrylate, butylmethacrylate, isobutylacrylate, hexylacrylate, isooctylacrylate, isobornylacrylate, isobornylmethacrylate, cyclohexylmethacrylate, 1,3-butanedioldiacrylate, 1,3-butanedioldimethacrylate, neopentylglycoldiacrylate, 1,4-butanedioldiacrylate, 1,4-butanedioldimethacrylate, 1,6-hexanedioldiacrylate, 1,6- hexanedioldimethacrylate, 1,9-nonanedioldimethacrylate, 1,10-decanedioldimethacrylate, dimethylol-tricyclodecanediacrylate, pentaerythritoltriacrylate, pentaerythritoltetraacrylate, pentaerythritoltrimethacrylate, pentaerythritoltetramethacrylate, dipentaerythritolhexaacrylate, dipentaerythritolhexamethacrylate, 2-hydroxyethylacrylate, 2-hydroxyethylmethacrylate, 1,3-diacryloyloxy-2-hydroxypropane, 1,3-dimethacryloyloxy-2-hydroxypropane, methylenebisacrylamide, N,N-dimethylacrylamide, N-methylolacrylamide, 2,2,6,6-tetramethyl piperidinyl methacrylate, 2,2,6,6-tetramethyl piperidinyl acrylate, N-methyl-2,2,6,6-tetramethyl piperidinyl methacrylate, N-methyl-2,2,6,6-tetramethyl piperidinyl acrylate, ethyleneoxyde modified bisphenol A diacrylate, ethylene oxyde modified bisphenol A dimethacrylate, N-vinylpyrrolidone, N-vinylcaprolactam and the like. One of these can be used alone, or two kinds or more can be used in combination.

Among these, particularly preferred examples for use include 1,9-nonanedioldimethacrylate, 1,10-decanedioldimethacrylate, dimethylol-tricyclodecanediacrylate, isobornylacrylate, isobornylmethacrylate, pentaerythritoltriacrylate, pentaerythritoltetraacrylate, pentaerythritoltrimethacrylate, pentaerythritoltetramethacrylate, dipentaerythritolhexaacrylate, dipentaerythritolhexamethacrylate, methylenebisacrylamide, N,N-dimethylacrylamide, N-methylolacrylamide, 2,2,6,6-tetramethylpiperidinylmethacrylate, 2,2,6,6-tetramethylpiperidinylacrylate, N-methyl-2,2,6,6-tetramethylpiperidinylmethacrylate, N-methyl-2,2,6,6-tetramethylpiperidinylacrylate, ethyleneoxyde modified bisphenol A diacrylate, ethyleneoxyde modified bisphenol A dimethacrylate, N-vinylpyrrolidone, N-vinylcaprolactam and the like.

The content of the photopolymerizable compound of the resin composition of the present invention is, with respect to 100 parts by mass of the heat-resistant resin, preferably 5 to 200 parts by mass, and more preferably 5 to 150 parts by mass from the viewpoint of the compatibility. With the content of the photopolymerizable compound of 5 parts by mass or more, the elution of the exposed portion during the development can be prevented, and a resin composition with a high residual film rate after the development can be obtained. Moreover, when the photopolymerizable compound has a content of 200 parts by mass or less, whitening of the film during the film formation can be prevented.

The resin composition of the present invention has preferably a viscosity of 2 to 5,000 mPa·s. The viscosity can be measured using an E rotational viscometer. By adjusting the solid content to achieve the viscosity of 2 mPa·s or more, a desired film thickness can be more easily obtained. On the other hand, when the viscosity is 5,000 mPa·s or less, a uniformly coated film can be more easily obtained. The resin composition with such a viscosity can be easily obtained by, for example, adjusting the solid content to 5 to 60% by mass.

A method of forming a heat-resistant resin pattern of a cured film using the resin composition of the present invention will be explained below.

First of all, the resin composition of the present invention is coated on a substrate. Examples of substrates include, but not limited to, silicon wafers, ceramics, gallium arsenide, organic circuit substrates, inorganic circuit substrates, composite substrates of a silicon wafer and an encapsulation resin such as an epoxy resin or the like, and those obtained by arranging constituent materials of the circuit on these substrates. Examples of the organic circuit substrates include glass substrate copper-clad laminates such as glass cloth and epoxy copper-clad laminates, composite copper-clad laminates such as glass nonwoven cloth and epoxy copper-clad laminates, temporary attachment carrier substrates, heat resistant and thermoplastic substrates such as polyetherimide resin substrates, polyether ketone resin substrates, and polysulfone resin substrates, and flexible substrates such as polyester copper-clad film substrates and polyimide copper-clad film substrates. Examples of the inorganic circuit substrates include ceramic substrates such as glass substrates, alumina substrates, aluminum nitride substrates, silicon carbide substrates, and metal substrates such as aluminum base substrates and iron base substrates. Examples of the constituent material of the circuit are conductors containing a metal such as silver, gold, copper, resistors containing an inorganic oxide or the like, low dielectric materials containing a glass material and/or a resin, high dielectric materials containing a resin, high dielectric inorganic particles or the like, insulators such as a glass material or the like. Examples of the coating methods include spin coating using a spinner, spray coating, roll coating, screen printing, blade coater, die coater, calender coater, meniscus coater, bar coater, roll coater, comma roll coater, gravure coater, screen coater, slit die coater and the like. The coated film thickness varies depending on the coating method, the solid content, the viscosity or the like of the composition. The coating is usually performed in a way that the film thickness after the drying will be 0.1 to 150 μm. In the case of a photosensitive uncured sheet, the drying and detachment follow.

In order to enhance the attachment of a substrate such as a silicon wafer with the resin composition, the substrate can be treated in advance with a silane coupling agent mentioned above. For example, a surface treatment is performed by spin coating, dipping, spray coating, a vapor treatment and the like with a solution dissolving 0.5 to 20% by mass of the above silane coupling agent in a solvent such as isopropanol, ethanol, methanol, water, tetrahydrofuran, propyleneglycolmonomethylether acetate, propyleneglycolmonomethylether, ethyl lactate, diethyl adipate or the like. In some cases, the reaction between the substrate and the silane coupling agent can be proceeded by carrying out a thermal treatment at 50° C. up to 300° C. afterwards.

Then, the substrate on which the resin composition or the uncured sheet has been coated or laminated is dried, and thus a photosensitive resin composition-coated film is obtained. Drying is preferably carried out at a temperature in the range of 50° C. to 150° C. for 1 minute to several hours, using an oven, a hot plate, infrared light or the like.

Then, this resin composition-coated film is irradiated with actinic rays through a mask having a desired pattern and thus subjected to exposure. The actinic rays used for the exposure include ultraviolet rays, visible rays, electron beams, X rays and the like, but in the present invention, the i-line (365 nm), h-line (405 nm) or g-line (436 nm) of a mercury lamp is preferably used.

In order to form a pattern, after the exposure, using a developing solution, the exposed portion is removed in the case of a positive-type and the unexposed portion is removed in the case of negative-type. The developing solution is preferably a solution of an alkaline compound such as tetramethylammonium hydroxide, diethanolamine, diethylaminoethanol, sodium hydroxide, potassium hydroxide, sodium carbonate, potassium carbonate, triethylamine, diethylamine, methylamine, dimethylamine, dimethylaminoethyl acetate, dimethylaminoethanol, dimethylaminoethyl methacrylate, cyclohexylamine, ethylene di-amine, hexamethylene di-amine, or the like. In some cases, one or a mixture of several kinds of polar solvents such as N-methyl- 2-pyrrolidone, N,N-dimethylformamide, N,N-dimethylacetamide, dimethylsulfoxide, γ-butyrolactone and dimethylacrylamide, alcohols such as methanol, ethanol and isopropanol, esters such as ethyl lactate and propyleneglycolmonomethylether acetate, ketones such as cyclopentanone, cyclohexanone, isobutylketone, and methylisobutylketone, and the like may be added to this alkali solution. Development can be carried out by spraying the above developing solution on the coated film side, dipping in a developing solution or applying ultrasonic waves while dipping, spraying the developing solution while rotating the substrate, or the like. The rinsing treatment with water is preferred after the development. In this case as well, an alcohol such as ethanol or isopropyl alcohol, or an ester such as ethyl lactate or propyleneglycolmonomethylether acetate may be added to the water for the rinsing treatment.

After the development, a temperature of 150° C. to 500° C. is applied to proceed with a crosslinking reaction. By crosslinking, the heat resistance and the chemical resistance can be further improved. As a method of this thermal treatment, a method of selecting a temperature and increasing the temperature stepwise, or selecting a temperature range and continuously increasing the temperature can be selected and carried out for 5 minutes to 5 hours. One example of the former case is a thermal treatment at 130° C. and 200° C. for 30 minutes for each. One example of the latter case is a method of linearly raising the temperature from room temperature to 400° C. over 2 hours. The curing condition in the present invention is preferably a temperature of 150° C. or higher and 350° C. or lower. Since the present invention aims to provide a cured film which is excellent particularly in a curing property at a low temperature, the temperature of 160° C. or higher and 250° C. or lower is more preferred and from the viewpoint of the influence on the semiconductor apparatus, the temperature of 160° C. or higher and 190° C. or lower is further preferred.

The heat-resistant resin-coated film formed from the resin composition of the present invention can be used for semiconductor apparatus and electronic components such as multilayer wire boards and the like, and organic EL display devices. Specifically, applications for a passivation film of a semiconductor, a surface protective film or an interlayer dielectric film of a semiconductor device, an interlayer dielectric film of a multilayer wires for high-density mounting, an interlayer dielectric film of an electronic component such as an inductor and a SAW filter, an interlayer dielectric layer and a flat layer of an organic electroluminescent element (organic EL) are suitable but the applications are not limited thereto and can have various structures.

An application example of the resin composition of the present invention into a semiconductor apparatus having a bump is explained with reference to figures. FIG. 1 shows an enlarged cross-sectional view of a pad portion of a semiconductor apparatus having a bump of the present invention. As shown in FIG. 1, the silicon wafer 1 has a passivation film 3 formed on an aluminum (hereinafter referred to as Al) pad 2 for input and output, and a via hole is formed in the passivation film 3. On the passivation film 3 is formed a dielectric film 4 as a pattern obtained from the resin composition of the present invention, and a metal (Cr, Ti or the like) film 5 is formed in connection with the Al pad 2, forming a metal wire (Al, Cu or the like) 6 by electrolytic plating or the like. The periphery of the solder bump 10 of the metal film 5 is subjected to etching to make each pad insulated with each other. On the insulated pads, a barrier metal 8 and a solder bump 10 are formed. The resin composition of the dielectric film 7 can be processed for a thick film in the scribe line 9. When a flexible component is introduced in the resin composition, the warpage of the wafer is small, allowing for a highly precise exposure and transportation of the wafer. In addition, since the resin composition of the present invention also has an excellent degree of elongation, the stress from the encapsulation resin during the mounting can be reduced because the resin itself deforms, and thus the damage of the bump, wire, and low-k layer is prevented, thereby providing a semiconductor apparatus with a high reliability.

Figure 2:
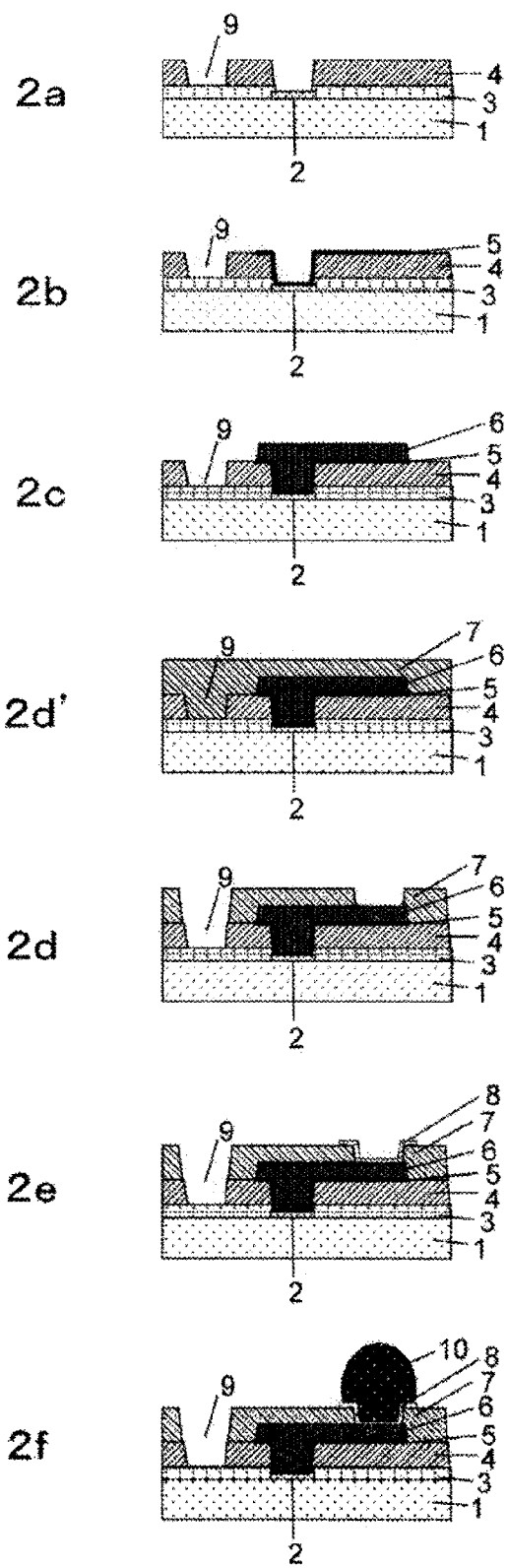
FIG. 2 shows in detail a method of producing a semiconductor apparatus having a bump.

The method of producing a semiconductor apparatus is explained in detail in FIG. 2. As shown in 2a of FIG. 2, on the silicon wafer 1, an Al pad 2 for input and output and a passivation film 3 are formed, and a dielectric film 4 as a pattern obtained from the resin composition of the present invention is formed. As shown in 2b of FIG. 2, a metal (Cr, Ti or the like) film 5 is formed in connection with the Al pad 2, forming, and as shown in 2c of FIG. 2, a metal wire 6 is formed by plating method. Then, as shown in 2d of FIG. 2, the resin composition of the present invention is coated, and after a photolithography step, the dielectric film 7 having a pattern shown in 2d of FIG. 2 is formed. On the dielectric film 7, an additional wire (so-called rewire) can be formed. When a multilayer wire structure of 2 layers or more is formed, the above steps can be repeated to form a multilayer wire structure in which the rewires of 2 layers or more are separated by the interlayer dielectric films obtained from the resin composition of the present invention. In this case, the formed dielectric films are exposed to various chemical solutions in a plurality of times, but since the dielectric films obtained from the resin composition of the present invention are excellent in the adhesion property and chemical resistance, a good multilayer wire structure can be formed. There is no upper limit in the number of layers in the multilayer wire structure, and those with 10 layers or less are often used.

Next, as shown in 2e and 2f of FIG. 2, the barrier metal 8 and the solder bump 10 are formed. The dicing is performed along the last scribe line 9 to divide each chip.

Figure 3:
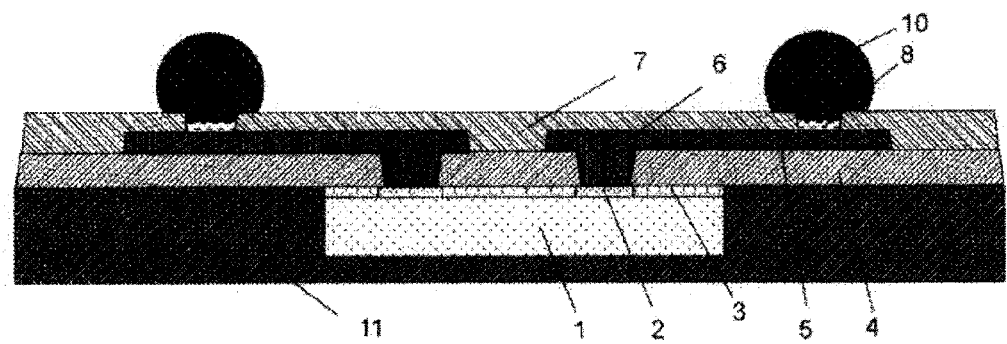
FIG. 3 is a cross sectional view of a production process of a semiconductor apparatus, showing an Example of the present invention.

An application example 2 of the resin composition of the present invention into a semiconductor apparatus having a bump is explained with reference to figures. FIG. 3 shows an enlarged cross-sectional view of a pad portion of a semiconductor apparatus having a dielectric film of the present invention and shows a structure called fan-out wafer level package (fan-out WLP). Similarly to the application example 1 described above, the silicon wafer 1 on which the Al pad 2 and the passivation film 3 are formed is subjected to dicing and cut for each chip and then sealed with the resin 11. Over across this encapsulation resin 11 and the chip, a dielectric film 4 is formed as a pattern obtained from the resin composition of the present invention, and a metal (Cr, Ti or the like) film 5 and a metal wire 6 are formed. Then, in the opening portion of the dielectric film 7 formed on the encapsulation resin outside the chip, the barrier metal 8 and the solder bump 10 are formed. Fan-out WLP is a semiconductor package in which an extended portion is provided around a semiconductor chip using an encapsulation resin such as an epoxy resin, a rewire is applied from the electrode on the semiconductor chip to the extended portion, and a solder ball is also mounted on the extended portion, thereby securing the necessary number of terminals. In fan-out WLPs, a wire is provided so as to straddle the boundary formed by the main surface of the semiconductor chip and the main surface of the encapsulation resin. In other words, an interlayer dielectric film is formed on a substrate composed of two or more kinds of materials, which are a semiconductor chip provided with a metal wire and an encapsulation resin, and a wire is formed on the interlayer dielectric film.

Figure 5:
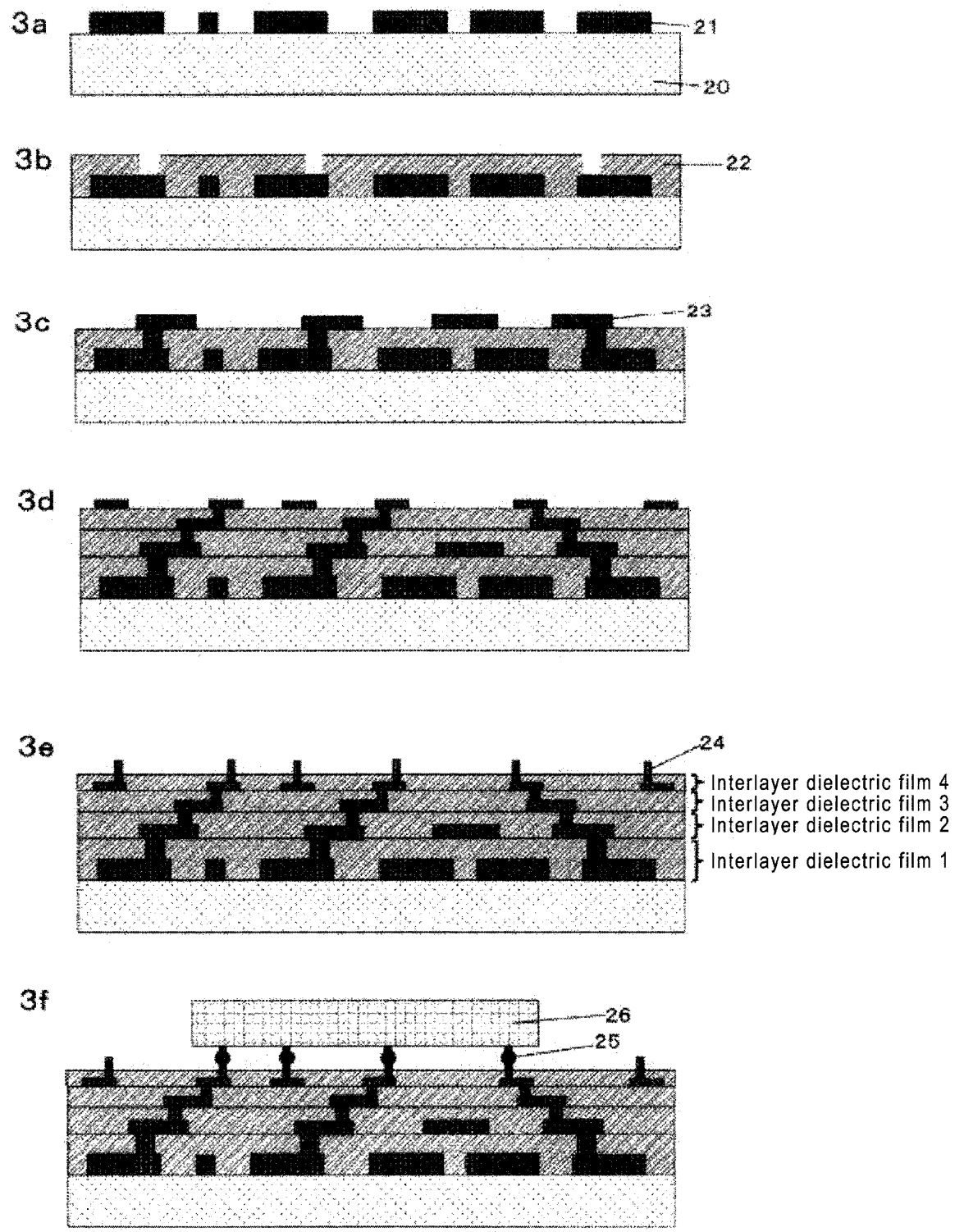
FIG. 5 shows a method of producing a semiconductor apparatus by RDL first.

In addition, as the fan-out WLP, there exists a type of package which is prepared by a step called RDL-first in which an interlayer dielectric film is arranged between rewires on the support substrate with a temporary attachment material disposed thereon, and after the silicon chip and the encapsulation resin are arranged on the support substrate, the support substrate with the temporary attachment material disposed and the rewires are separated. In this type of package, since a glass substrate or the like which is easier to warp than a silicon wafer is often used as the support substrate, the dielectric film has preferably a low stress. A method of producing a semiconductor apparatus by RDL first is described with reference to FIG. 5. In 3a of FIG. 5, a barrier metal such as Ti is formed on the support substrate 20 by a sputtering method and then a Cu seed (seed layer) is formed thereon by a sputtering method, and then an electrode pad 21 is formed by a plating method. In the subsequent step 3b, the photosensitive resin composition of the present invention is coated, subjected to the photolithography step, and thus a pattern-formed dielectric film 22 is formed. In the step 3c, the seed layer is again formed by a sputtering method, and a metal wire 23 (rewire layer) is formed by a plating method. Subsequently, in order to match the pitch of the conducting portion of the semiconductor chip with the pitch of the metal wire, the steps 3b and 3c are repeated to form a multilayer wire structure as shown in 3d. In the subsequent step 3e, the photosensitive resin composition of the present invention is again coated, subjected to the photolithography step, and thus a pattern-formed dielectric film is formed. Then, a Cu post 24 is formed by a plating method. The pitch of the Cu post and the pitch of the conducting portion of the semiconductor chip are equal. That is, in order to make a multilayered rewire layer while narrowing the pitch of the metal wire, as shown in 3e of FIG. 3, the film thickness of the interlayer dielectric films is in the following order: the interlayer dielectric film 1>the interlayer dielectric film 2>the interlayer dielectric film 3>the interlayer dielectric film 4>. In the step 3f, the semiconductor chip 26 is connected via solder bumps 25, so that a semiconductor apparatus having a multilayer wire structure by RDL first can be obtained.

Other than this, in a type of semiconductor package in which a semiconductor chip is embedded in a recess portion formed in a glass epoxy resin substrate, a wire is provided so as to straddle the boundary between the main surface of the semiconductor chip and the main surface of the printed circuit substrate. In this aspect as well, an interlayer dielectric film is formed on a substrate composed of two or more kinds of materials, and a wire is formed on the interlayer dielectric film. Because the cured film obtained by curing the resin composition of the present invention shows a high degree of elongation and a high adhesion capacity to a semiconductor chip provided with a metal wire as well as to an encapsulation resin such as an epoxy resin or the like, the cured film is used suitably as an interlayer dielectric film provided on a substrate composed of two or more kinds of materials.

Further, in the fan-out WLP, the refinement of rewires has been advanced. The cured film of the resin composition of the present invention also has a high metal adhesion property to metal wires in which a distance between adjacent wires is 5 μm or less, and therefore is suitably used for fine rewires. With this structure, as the rewire layer approaches the semiconductor chip, the width of the metal wires and the distance between adjacent wires gets narrower, and as the interlayer dielectric film approaches the semiconductor chip, the thickness thereof gets smaller. Thus, this structure responds well to high integration of chips. For this reason, along with the increase in resolution, in-plane uniformity on rewires having a difference in level is an important issue.

Figure 4:
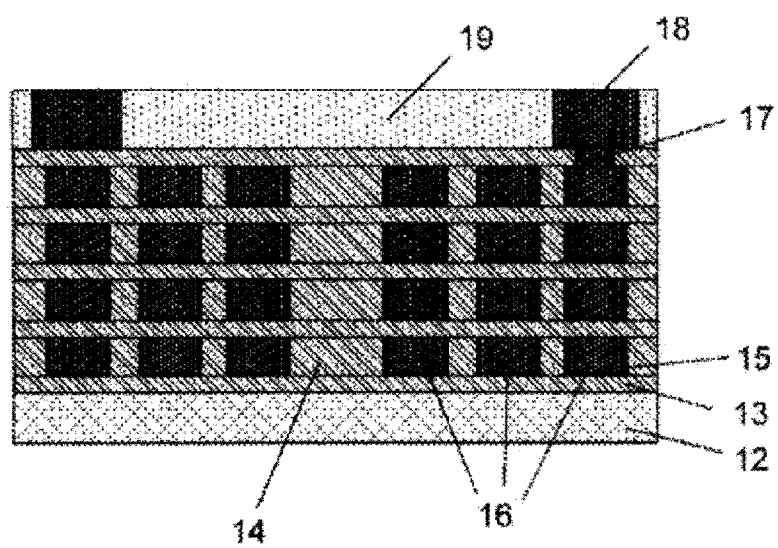
FIG. 4 is a cross sectional view of a coil component of an inductor device, showing an Example of the present invention.

An application example 3 of the resin composition of the present invention into a coil component of an inductor device is explained with reference to figures. FIG. 4 is a cross sectional view of a coil component having a dielectric film of the present invention. As shown in FIG. 3, a dielectric film 13 is formed on the substrate 12, and a dielectric film 14 is formed thereon as a pattern. Ferrite or the like is used as the substrate 12. The resin composition of the present invention may be used for either the dielectric film 13 or the dielectric film 14. A metal (Cr, Ti or the like) film 15 is formed in the opening portion of this pattern, and a metal wire (Ag, Cu or the like) 16 is plated thereon. The metal wire 16 (Ag, Cu, or the like) is formed on a spiral. The steps of 13 to 16 are repeated in a plurality of times and subjected to lamination, resulting in a function as a coil. Finally, the metal wire 16 (Ag, Cu, or the like) is connected to the electrode 18 by the metal wire 17 (Ag, Cu, or the like) and is sealed with the encapsulation resin 19.

The resin composition of the present invention is also suitably used for an organic EL display device. The organic EL display device has a driving circuit, a planarizing layer, a first electrode, a dielectric layer, a light emitting layer, and a second electrode on a substrate, and the planarizing layer and/or the dielectric layer is formed from the cured film of the present invention. The organic EL light-emitting materials are susceptible to degradation by moisture and may cause adverse effects such as reduction of the ratio of the area of light-emitting portion to the area of light-emitting pixels, but since the cured film of the present invention has a low ratio of absorption of water, stable driving and light emission properties can be obtained. In an active matrix type display device as an example, a TFT and a wire positioned on the side of the TFT and connected to the TFT are formed on a substrate of glass, various plastics or the like, and irregularities are covered thereon, forming a planarizing layer, and a display element is provided on the planarizing layer. The display element and the wire are connected via a contact hole formed in the planarizing layer.

Figure 6:
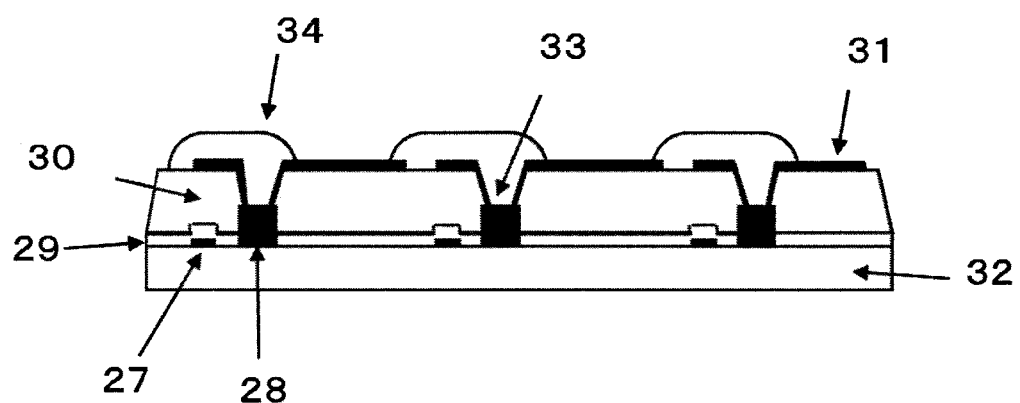
FIG. 6 is a cross sectional view of one example of a TFT substrate.

FIG. 6 is a cross sectional view of one example of a TFT substrate. A bottom gate type or top gate type TFT (thin film transistor) is provided in a matrix on the substrate 32, and a dielectric layer 29 is formed and covers the TFT 27. On the dielectric layer 29, a wire 28 connected to the TFT 27 is provided. Furthermore, on the dielectric layer 29, the planarizing layer 30 is provided in a way that the wire 28 is embedded. In the planarizing layer 30, a contact hole 33 reaching the wire 28 is provided. Then, the ITO (transparent electrode) 31 is formed on the planarizing layer 30 in a way that the wire 28 is connected via the contact hole 33. The ITO 31 herein is an electrode of a display element (for example, an organic EL element). Then, the dielectric layer 34 is formed and covers the periphery of the ITO 31. The organic EL element may be a top emission type in which emitted light comes from the side opposite to the substrate 32 or a bottom emission type in which the light is extracted from the side of the substrate 32. In this way, an active matrix type organic EL display device in which the TFT 27 is connected to each organic EL element for driving the organic EL element is obtained.

Such a dielectric layer 29, planarizing layer 30 and/or dielectric layer 34 can be formed, as described above, by a step of forming a photosensitive resin film from the resin composition or resin sheet of the present invention, a step of exposing the photosensitive resin film to light, a step of developing the exposed photosensitive resin film, and a step of thermally treating the developed photosensitive resin film. An organic EL display device can be obtained from a production method having these steps.

EXAMPLES

The present invention is explained below by way of Examples, but the present invention is not limited to these Examples. First, evaluation methods in each Example and Comparative Example are explained. For the evaluation, a resin composition (hereinafter referred to as varnish) which had been filtered beforehand with a 1-μm filter made of polytetrafluoroethylene (manufactured by Sumitomo Electric Industries, Ltd.) was used.

(1) Measurement of the Weight Average Molecular Weight

The molecular weight of the heat-resistant resin was measured with a GPC (gel permeation chromatography) apparatus Waters 2690-996 (manufactured by Nihon Waters K.K.), using as a developing solvent N-methyl-2-pyrrolidone (hereinafter referred to as NMP), and the weight average molecular weight (Mw) was calculated based on polystyrene.

(2) The Ratio of the Cyclization of Polyhydroxyamide and the Ratio of Polyimidization To calculate the ratio of cyclization, a varnish was spin-coated on a silicon wafer and dried at 120° C. for 3 minutes to obtain a coating film having a film thickness of 5 μm. The coated film was heated at 180° C. for 10 minutes or at 300 to 350° C. for 10 minutes to obtain a cured film (cured film (A) heated at 180° C. and cured film (B) heated at 300 to 350° C.). The infrared absorption spectrum of the cured film (A) and the cured film (B) was measured, and the absorbance of the peak due to C—O stretching vibration in the vicinity of 1050 $cm^{-1}$ was determined. The ratio of cyclization of the cured film (A) was calculated with the ratio of cyclization of the polyhydroxyamide of the cured film (B) taken as 100%.

Since the solubility at the time of thermal curing is suppressed and the effect of high chemical resistance is obtained, the ratio of cyclization of polyhydroxyamide is preferably 30% or more.

As the imidization ratio, the absorbance of C near the absorption peak (1377 $cm^{-1}$) of the imide structure due to polyimide was determined. The imidization ratio of the cured film (A) was calculated with the imidization ratio of the cured film (B) taken as 100%.

Since the solubility during the thermal curing is suppressed and the high chemical resistance effect can be obtained, the imidization ratio is preferably 50% or more, and more preferably 80% or more.

(3) Evaluation of Chemical Resistance

The varnish was coated on 6-inch silicon wafers. The coating and developing apparatus Mark-7 was used to prebake the coated wafers at 120° C. for 3 minutes to achieve the film thickness of 11 μm. As a coating method, a spincoat method was used. After prebaking, the temperature was raised to 180° C. in increments of 3.5° C./min at an oxygen concentration of 20 ppm or less, using an inert oven CLH-21CD-S (manufactured by Koyo Thermo System Co., Ltd.) and a thermal treatment at 180° C. was carried out for 1 hour. When the temperature was 50° C. or less, the wafers were taken out to measure the film thickness. After that, the wafers were dipped in a resist stripper ST-120 (TOKYO OHKA KOGYO CO., LTD.) at 60° C. for 30 minutes. After the wafers were taken out from the solvent and washed with purified water, the film thickness was measured again. When the absolute value of the variation ratio was more than 20% or when the cured film was detached, the wafers were evaluated as poor (C), wafers with a variation ratio of more than 10% and 20% or less were evaluated as fair (B), and wafers with a variation ratio of 10% or less were evaluated as very good (A).

(4) Evaluation of the Degree of Elongation (High Degree of Elongation)

The varnish was coated by a spincoat method on 8-inch silicon wafers and prebaked, using a coating and developing apparatus ACT-8 to achieve a film thickness of 11 μm after prebaking at 120° C. for 3 minutes. Then, the temperature was raised to 190° C. in increments of 3.5° C./min at an oxygen concentration of 20 ppm or less, using an inert oven CLH-21CD-S (manufactured by Koyo Thermo System Co., Ltd.) and a thermal treatment at 180° C. was carried out for 1 hour. When the temperature was 50° C. or less, the wafers were taken out and dipped in 45% by mass hydrofluoric acid for 5 minutes to peel off the film of the resin composition from the wafer. This film was cut into strips having a width of 1 cm and a length of 9 cm and subjected to tension at a tension rate of 50 mm/min at a room temperature of 23.0° C. and a humidity of 45.0% RH, using a TENSILON RTM-100 (manufactured by Orientec Co., Ltd.), and the degree of elongation at break was measured. For the measurement, 10 strips per sample were measured, and the average value of the top 5 scores was obtained from the results. The degree of elongation at break of 90% or more was considered as excellent (A), of 70% or more and less than 90% as good (B), of 40% or more and less than 70% as fair (C), of less than 40% as poor (D).

Synthesis Example 1 Synthesis of a Di-Amine Compound (A-1) Represented by the General Formula (1)

Bis(3-amino-4-hydroxyphenyl)hexafluoropropane (18.3 g, 0.05 mol) was dissolved in 100 ml of acetone and 17.4 g (0.3 mol) of propylene oxide, and the solution was cooled to −15° C. To this mixture, a solution of 20.41 g (0.11 mol) of 2-(4-nitrophenoxy)acetyl chloride dissolved in 100 ml of acetone was added dropwise. After the completion of the dropwise addition, the mixture was allowed to react at −15° C. for 4 hours, then the temperature was returned to room temperature. The solution was concentrated on a rotary evaporator and the resulting solid was recrystallized from a solution of tetrahydrofuran and ethanol.

The solid collected by recrystallization was dissolved in 100 ml of ethanol and 300 ml of tetrahydrofuran, and 2 g of 5% palladium-carbon was added. The mixture was vigorously stirred. To this mixture, hydrogen was introduced by a balloon and the reduction reaction was carried out at room temperature. After about 2 hours, it was confirmed that the balloon did not deflate anymore, and the reaction was terminated. After the completion of the reaction, the palladium compound which was a catalyst was removed by filtration, and the mixture was concentrated in a rotary evaporator to obtain a di-amine (A-1).

FT-IR/$cm^{-1}$: 3350 to 3005, 2938, 2875, 1650, 1604, 1550, 1501, 1420, 1299, 1130, 820.

$^1$H-NMR (DMSO): δ (ppm): 10.3 (s, 2H), 9.2 (s, 2H), 8.0 (s, 2H), 6.5-6.9 (m, 12H), 4.6 (s, 4H), 4.2 (s, 4H).

Synthesis Example 2 Synthesis of a Di-Amine Compound (A-2) Represented by the General Formula (1)

Bis(3-amino-4-hydroxyphenyl)hexafluoropropane (18.3 g, 0.05 mol) was dissolved in 100 ml of acetone and 17.4 g (0.3 mol) of propylene oxide, and the solution was cooled to −15° C. To this mixture, a solution of 26.6 g (0.11 mol) of 6-(4-nitrophenoxy)hexanoyl chloride dissolved in 100 ml of acetone was added dropwise. After the completion of the dropwise addition, the mixture was allowed to react at −15° C. for 4 hours, then the temperature was returned to room temperature. The solution was concentrated on a rotary evaporator and the resulting solid was recrystallized from a solution of tetrahydrofuran and ethanol.

The solid collected by recrystallization was dissolved in 100 ml of ethanol and 300 ml of tetrahydrofuran, and 2 g of 5% palladium-carbon was added. The mixture was vigorously stirred. To this mixture, hydrogen was introduced by a balloon and the reduction reaction was carried out at room temperature. After about 2 hours, it was confirmed that the balloon did not deflate anymore, and the reaction was terminated. After the completion of the reaction, the palladium compound which was a catalyst was removed by filtration, and the mixture was concentrated in a rotary evaporator to obtain a di-amine (A-2).

FT-IR/cm$^{-1}$: 3350 to 3005, 2940, 2880, 1650, 1604, 1550, 1501, 1420, 1299, 1130, 820.

$^1$H-NMR (DMSO): δ (ppm): 10.3 (s, 2H), 9.2 (s, 2H), 8.0 (s, 2H), 6.5-6.9 (m, 12H), 4.6 (s, 4H), 3.8 (t, 4H), 2.5 (t, 4H), 1.4-1.7 (m, 12H).

Synthesis Example 3 Synthesis of a Di-Amine Compound (A-3) Represented by the General Formula (1)

Bis(3-amino-4-hydroxyphenyl)hexafluoropropane (18.3 g, 0.05 mol) was dissolved in 100 ml of acetone and 17.4 g (0.3 mol) of propylene oxide, and the solution was cooled to −15° C. To this mixture, a solution of 26.1 g (0.11 mol) of 3-(1,3-dioxoisoindolin-2-yl)propanoyl chloride dissolved in 100 ml of acetone was added dropwise. After the completion of the dropwise addition, the mixture was allowed to react at −15° C. for 4 hours, then the temperature was returned to room temperature. The solution was concentrated on a rotary evaporator and the resulting solid was recrystallized from a solution of tetrahydrofuran and ethanol.

The solid collected by recrystallization was dissolved in 400 ml of ethanol and refluxed under a nitrogen atmosphere. To this suspension, a solution of 3.76 g (0.06 mmol) of 80% hydrazine monohydrate in 10 ml of ethanol was added dropwise over 15 minutes and then refluxed for 4 hours. The reaction solution was cooled to room temperature and filtered, and the filtrate (white powder, phthalic hydrazide as a main component) was rinsed once with 25 ml of ethanol and twice with 50 ml of ethanol, and the filtrate and the rinsing solution were combined. Since slight turbidity was observed in this solution, the solution was filtered to obtain a purified solution. This filtrate was concentrated in a rotary evaporator to obtain a di-amine (A-3).

FT-IR/cm$^{-1}$: 3350 to 3005, 2943, 2900, 1650, 1604, 1550, 1501, 1420, 1299, 1130, 820.

$^1$H-NMR (DMSO): δ (ppm): 10.3 (s, 2H), 9.2 (s, 2H), 8.0 (s, 2H), 6.5-6.9 (m, 4H), 4.6 (s, 4H), 4.0 (m, 4H), 2.5 (t, 4H).

Synthesis Example 4 Synthesis of Polyimide Precursor (I)

Under a dry nitrogen stream, 33.21 g (0.05 mol) of (A-1) obtained in Synthesis Example 1 was dissolved in 80 g of N-methyl-2-pyrrolidone (NMP). To this mixture, 13.95 g (0.045 mol) of 3,3',4,4'-diphenyl ether tetracarboxylic anhydride (ODPA) was added together with 10 g of NMP and reacted at 40° C. for 1 hour. Further, 1.64 g (0.01 mol) of 5-norbornene-2,3-dicarboxylic anhydride (NA) was added as an end cap compound, and the mixture was reacted at 40° C. for 1 hour. Thereafter, a solution prepared by diluting 12.50 g (0.11 mol) of N,N'-dimethylformamide dimethyl acetal with 15 g of NMP was added dropwise over 10 minutes. After the dropwise addition, the mixture was stirred at 40° C. for 2 hours. After the reaction ended, the solution was poured into 2 L of water, and a polymer precipitate was obtained by filtration. The polymer solid was dried in a vacuum drier at 50° C. for 72 hours to obtain a polyimide precursor (I). The weight average molecular weight was 32,300.

Synthesis Example 5 Synthesis of Polyimide Precursor (II)

Under a dry nitrogen stream, 34.63 g (0.05 mol) of (A-2) obtained in Synthesis Example 2 was dissolved in 80 g of N-methyl-2-pyrrolidone (NMP). To this mixture, 13.95 g (0.045 mol) of 3,3',4,4'-diphenyl ether tetracarboxylic anhydride (ODPA) was added together with 10 g of NMP and reacted at 40° C. for 1 hour. Further, 1.64 g (0.01 mol) of 5-norbornene-2,3-dicarboxylic anhydride (NA) was added as an end cap compound, and the mixture was reacted at 40° C. for 1 hour. Thereafter, a solution prepared by diluting 12.50 g (0.11 mol) of N,N'-dimethylformamide dimethyl acetal with 15 g of NMP was added dropwise over 10 minutes. After the dropwise addition, the mixture was stirred at 40° C. for 2 hours. After the reaction ended, the solution was poured into 2 L of water, and a polymer precipitate was obtained by filtration. The polymer solid was dried in a vacuum drier at 50° C. for 72 hours to obtain a polyimide precursor (II). The weight average molecular weight was 35,300.

Synthesis Example 6 Synthesis of Polyimide Precursor (III)

Under a dry nitrogen stream, 25.41 g (0.05 mol) of (A-3) obtained in Synthesis Example 3 was dissolved in 80 g of N-methyl-2-pyrrolidone (NMP). To this mixture, 13.95 g (0.045 mol) of 3,3',4,4'-diphenyl ether tetracarboxylic anhydride (ODPA) was added together with 10 g of NMP and reacted at 40° C. for 1 hour. Further, 1.64 g (0.01 mol) of 5-norbornene-2,3-dicarboxylic anhydride (NA) was added as an end cap compound, and the mixture was reacted at 40° C. for 1 hour. Thereafter, a solution prepared by diluting 12.50 g (0.11 mol) of N,N'-dimethylformamide dimethyl acetal with 15 g of NMP was added dropwise over 10 minutes. After the dropwise addition, the mixture was stirred at 40° C. for 2 hours. After the reaction ended, the solution was poured into 2 L of water, and a polymer precipitate was obtained by filtration. The polymer solid was dried in a vacuum drier at 50° C. for 72 hours to obtain a polyimide precursor (III). The weight average molecular weight was 29,400.

Synthesis Example 7 Synthesis of Polyhydroxyamide (IV)

Under a dry nitrogen gas stream, 34.63 g (0.05 mol) of (A-2) obtained in Synthesis Example 2 was dissolved in 100 g of NMP. To this mixture, an acid A (13.51 g, 0.045 mol) and 1.64 g (0.01 mol) of 5-norbornene-2,3-dicarboxylic anhydride (NA) were added together with 25 g of NMP, and reacted at 85° C. for 3 hours. After the reaction ended, the mixture was cooled to a room temperature, and acetic acid (13.20 g, 0.25 mol) was added with 25 g of NMP, and the mixture was stirred at room temperature for 1 hour. After the stirring ended, the solution was poured into 1.5 L of water, and a white precipitate was obtained. This precipitate was collected by filtration, washed 3 times with water, and dried in a circulation dryer at 50° C. for 3 days to obtain polyhydroxyamide (IV). The weight average molecular weight was 37,400.

Synthesis Example 8 Synthesis of Polyhydroxyamide-Polyimide Copolymer (V)

Under a dry nitrogen gas stream, 34.63 g (0.05 mol) of (A-2) obtained in Synthesis Example 2 was dissolved in 100 g of NMP. To this mixture, an acid A (6.76 g, 0.023 mol) and 6.98 g (0.023 mol) of ODPA, 1.64 g (0.01 mol) of 5-norbornene-2,3-dicarboxylic anhydride (NA) were added together with 25 g of NMP, and reacted at 85° C. for 3 hours. After the reaction ended, the mixture was cooled to a room temperature, and acetic acid (13.20 g, 0.25 mol) was added with 25 g of NMP, and the mixture was stirred at room temperature for 1 hour. After the stirring ended, the solution was poured into 1.5 L of water, and a white precipitate was obtained. This precipitate was collected by filtration, washed 3 times with water, and dried in a circulation dryer at 50° C. for 3 days to obtain polyhydroxyamide-polyimide copolymer (V). The weight average molecular weight was 35,500.

Synthesis Example 9 Synthesis of Polyhydroxyamide-Polyimide Copolymer (VI)

Under a dry nitrogen gas stream, 17.32 g (0.025 mol) of (A-2) obtained in Synthesis Example 2 and 9.16 g (0.025 mol) of BAHF were dissolved in 100 g of NMP. To this mixture, an acid A (6.76 g, 0.023 mol) and 6.98 g (0.023 mol) of ODPA, 1.64 g (0.01 mol) of 5-norbornene-2,3-dicarboxylic anhydride (NA) were added together with 25 g of NMP, and reacted at 85° C. for 3 hours. After the reaction ended, the mixture was cooled to a room temperature, and acetic acid (13.20 g, 0.25 mol) was added with 25 g of NMP, and the mixture was stirred at room temperature for 1 hour. After the stirring ended, the solution was poured into 1.5 L of water, and a white precipitate was obtained. This precipitate was collected by filtration, washed 3 times with water, and dried in a circulation dryer at 50° C. for 3 days to obtain polyhydroxyamide-polyimide copolymer (VI). The weight average molecular weight was 37,200, and 1.9.

Synthesis Example 10 Synthesis of Polyhydroxyamide-Polyimide Copolymer (VII)

Under a dry nitrogen gas stream, 17.32 g (0.025 mol) of (A-2) obtained in Synthesis Example 2, 7.33 g (0.020 mol) of BAHF and RT-1000 (5.0 g, 0.005 mol) were dissolved in 100 g of NMP. To this mixture, an acid A (6.76 g, 0.023 mol) and 6.98 g (0.023 mol) of ODPA, 1.64 g (0.01 mol) of 5-norbornene-2,3-dicarboxylic anhydride (NA) were added together with 25 g of NMP, and reacted at 85° C. for 3 hours. After the reaction ended, the mixture was cooled to a room temperature, and acetic acid (13.20 g, 0.25 mol) was added with 25 g of NMP, and the mixture was stirred at room temperature for 1 hour. After the stirring ended, the solution was poured into 1.5 L of water, and a white precipitate was obtained. This precipitate was collected by filtration, washed 3 times with water, and dried in a circulation dryer at 50° C. for 3 days to obtain polyhydroxyamide-polyimide copolymer (VII). The weight average molecular weight was 39,200.

Synthesis Example 11 Synthesis of Polyimide Precursor (VIII)

Under a dry nitrogen gas stream, 18.31 g (0.05 mol) of BAHF was dissolved in 80 g of N-methyl-2-pyrrolidone (NMP). To this mixture, 13.95 g (0.045 mol) of 3,3',4,4'-diphenyl ether tetracarboxylic anhydride (ODPA) was added together with 10 g of NMP and reacted at 40° C. for 1 hour. Further, 1.64 g (0.01 mol) of 5-norbornene-2,3-dicarboxylic anhydride (NA) was added as an end cap compound, and the mixture was reacted at 40° C. for 1 hour. Thereafter, a solution prepared by diluting 12.50 g (0.11 mol) of N,N'-dimethylformamide dimethyl acetal with 15 g of NMP was added dropwise over 10 minutes. After the dropwise addition, the mixture was stirred at 40° C. for 2 hours. After the reaction ended, the solution was poured into 2 L of water, and a polymer precipitate was obtained by filtration. The polymer solid was dried in a vacuum drier at 50° C. for 72 hours to obtain a polyimide precursor (VIII). The weight average molecular weight was 29,500.

Synthesis Example 12 Synthesis of Polyimide Precursor (IX)

Under a dry nitrogen stream, 30.23 g (0.05 mol) of HFHA was dissolved in 80 g of N-methyl-2-pyrrolidone (NMP). To this mixture, 13.95 g (0.045 mol) of 3,3',4,4'-diphenyl ether tetracarboxylic anhydride (ODPA) was added together with 10 g of NMP and reacted at 40° C. for 1 hour. Further, 1.64 g (0.01 mol) of 5-norbornene-2,3-dicarboxylic anhydride (NA) was added as an end cap compound, and the mixture was reacted at 40° C. for 1 hour. Thereafter, a solution prepared by diluting 12.50 g (0.11 mol) of N,N'-dimethylformamide dimethyl acetal with 15 g of NMP was added dropwise over 10 minutes. After the dropwise addition, the mixture was stirred at 40° C. for 2 hours. After the reaction ended, the solution was poured into 2 L of water, and a polymer precipitate was obtained by filtration. The polymer solid was dried in a vacuum drier at 50° C. for 72 hours to obtain a polyimide precursor (IX). The weight average molecular weight was 29,500.

Synthesis Example 13 Synthesis of Polyhydroxyamide (X)

Under a dry nitrogen gas stream, 18.31 g (0.05 mol) of BAHF was dissolved in 100 g of NMP. To this mixture, 14.67 g (0.045 mol) of dodecanedioic acid dichloride (acid B) was added together with 25 g of NMP and reacted at 85° C. for 3 hours. After the reaction ended, the mixture was cooled to a room temperature, and acetic acid (13.20 g, 0.25 mol) was added with 25 g of NMP, and the mixture was stirred at room temperature for 1 hour. After the stirring ended, the solution was poured into 1.5 L of water, and a white precipitate was obtained. This precipitate was collected by filtration, washed 3 times with water, and dried in a circulation dryer at 50° C. for 3 days to obtain polyhydroxyamide (X). The weight average molecular weight was 31,400.

Di-amines (A-1), (A-2), (A-3), HFHA and the acid A used in the synthesis examples are as follows.

Synthesis Example 14 Synthesis of a Di-Amine Compound (A-4) Represented by the General Formula (1)

Bis(3-amino-4-hydroxyphenyl)hexafluoropropane (18.3 g, 0.05 mol) was dissolved in 100 ml of acetone and 17.4 g (0.3 mol) of propylene oxide, and the solution was cooled to −15° C. To this mixture, a solution of 40.6 g (0.11 mol) of 3-(2-(2-(2-(1,3-dioxoisoindolin-2-yl)ethoxy)ethoxy)ethoxy) propyl chloride dissolved in 100 ml of acetone was added dropwise. After the completion of the dropwise addition, the mixture was allowed to react at −15° C. for 4 hours, then the temperature was returned to room temperature. The solution was concentrated on a rotary evaporator and the resulting solid was recrystallized from a solution of tetrahydrofuran and ethanol.

The solid collected by recrystallization was dissolved in 400 ml of ethanol and refluxed under a nitrogen atmosphere. To this suspension, a solution of 3.76 g (0.06 mmol) of 80% hydrazine monohydrate in 10 ml of ethanol was added dropwise over 15 minutes and then refluxed for 4 hours. The reaction solution was cooled to room temperature, filtered and the filtrate (white powder, phthalic hydrazide as a main component) was rinsed once with 25 ml of ethanol and twice with 50 ml of ethanol, and the filtrate and the rinsing solution were combined. Since slight turbidity was observed in this solution, the solution was filtered to obtain a purified solution. This filtrate was concentrated in a rotary evaporator to obtain a di-amine (A-4).

FT-IR/cm$^{-1}$: 3350 to 3005, 2943, 2900, 1650, 1604,1550, 1501, 1420, 1299, 1130, 820.

$^1$H-NMR (DMSO): δ (ppm): 10.3 (s, 2H), 9.2 (s, 2H), 8.0 (s, 2H), 6.5-6.9 (m, 4H), 4.6 (s, 4H), 4.3-4.5 (4.0 (m, 24H), 2.3 (t, 4H).

Synthesis Example 15 Synthesis of Polyimide Precursor (XI)

Under a dry nitrogen gas stream, 38.61 g (0.05 mol) of (A-4) obtained in Synthesis Example 14 was dissolved in 80 g of N-methyl-2-pyrrolidone (NMP). To this mixture, 13.95 g (0.045 mol) of 3,3',4,4'-diphenyl ether tetracarboxylic anhydride (ODPA) was added together with 10 g of NMP and reacted at 40° C. for 1 hour. Further, 1.64 g (0.01 mol) of 5-norbornene-2,3-dicarboxylic anhydride (NA) was added as an end cap compound, and the mixture was reacted at 40° C. for 1 hour. Thereafter, a solution prepared by diluting 12.50 g (0.11 mol) of N,N'-dimethylformamide dimethyl acetal with 15 g of NMP was added dropwise over 10 minutes. After the dropwise addition, the mixture was stirred at 40° C. for 2 hours. After the reaction ended, the solution was poured into 2 L of water, and a polymer precipitate was obtained by filtration. The polymer solid was dried in a vacuum drier at 50° C. for 72 hours to obtain a polyimide precursor (III). The weight average molecular weight was 45,300.

[Chem 29]

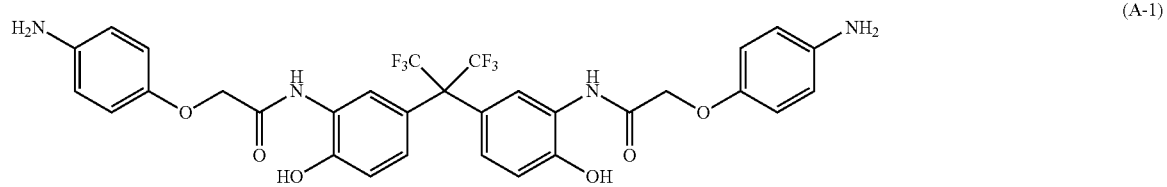

(A-1)

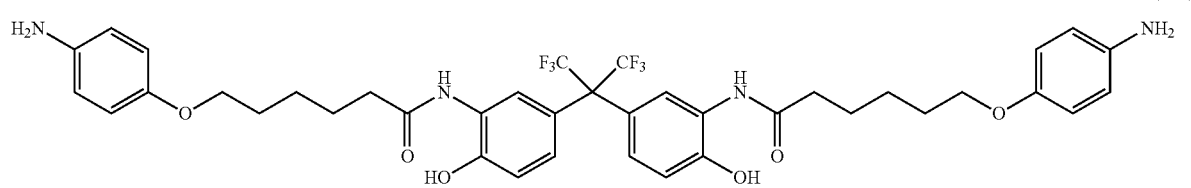

(A-2)

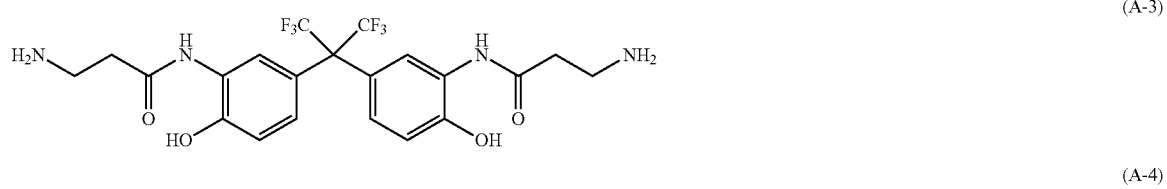

(A-3)

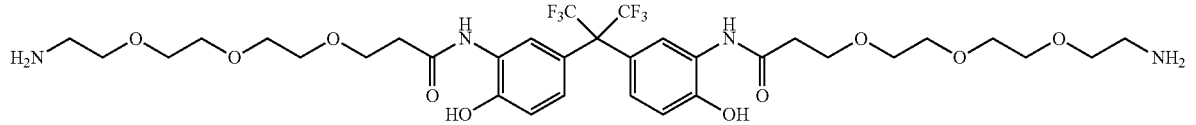

(A-4)

-continued

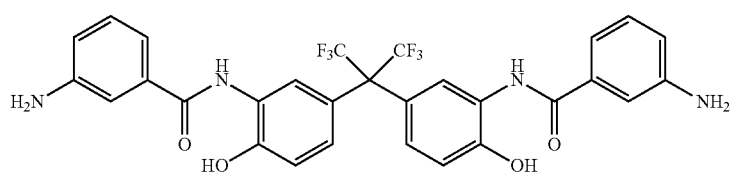

HFHA

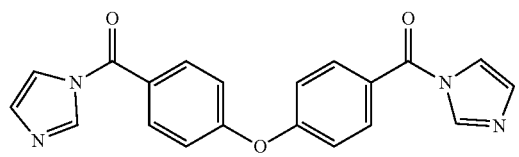

Acid A

Examples 1 to 8, Comparative Examples 1 to 3

To 10 g of the above resins (I) to (XI), 2.0 g of a photosensitive compound, 3.0 g of a thermal crosslinking agent and 20 g of γ-butyrolactone as a solvent were added to prepare a varnish.

The photosensitive compounds and the thermal crosslinking agents used in the examples are as follows.

[Chem 30]

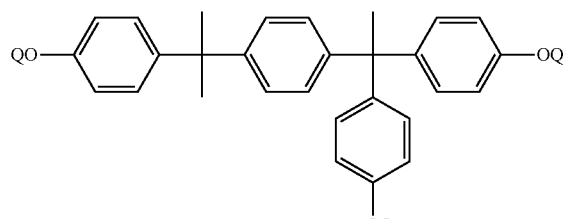

Photosensitive compound

-continued

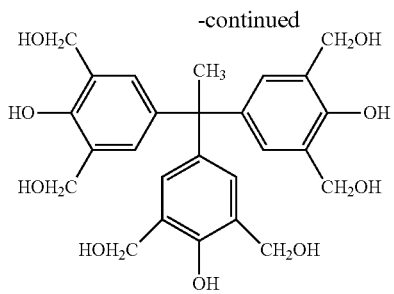

Thermal crosslinking agent

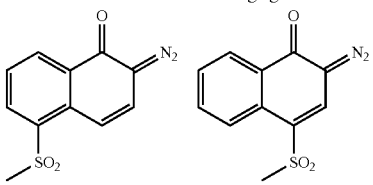

2:1

The raw materials and the composition of the resin in each Example and Comparative Example are shown in Table 1 and the evaluation results of the obtained resin compositions are shown in Table 2.

TABLE 1

| | | Raw materials and composition of resin | | | | | | | | | | |
|---|---|---|---|---|---|---|---|---|---|---|---|---|
| | | Di-amine component (mole ratio) | | | | | | | Acid component (mole ratio) | | Dianhydride (mole ratio) | Anhydride (mole ratio) |
| | Resin | (A-1) | (A-2) | (A-3) | (A-4) | BAHF | HFHA | RT-1000 | Acid A | Acid B | ODPA | NA |
| Example 1 | I | 100 | — | — | — | — | — | — | — | — | 90 | 20 |
| Example 2 | II | — | 100 | — | — | — | — | — | — | — | 90 | 20 |
| Example 3 | III | — | — | 100 | — | — | — | — | — | — | 90 | 20 |
| Example 4 | IV | — | 100 | — | — | — | — | — | 90 | — | — | 20 |
| Example 5 | V | — | 100 | — | — | — | — | — | 45 | — | 45 | 20 |
| Example 6 | VI | — | 50 | — | — | 50 | — | — | 45 | — | 45 | 20 |
| Example 7 | VII | — | 50 | — | — | 40 | — | 10 | 45 | — | 45 | 20 |
| Example 8 | XI | — | — | — | 100 | — | — | — | — | — | 90 | 20 |
| Comparative Example 1 | VIII | — | — | — | — | 100 | — | — | — | — | 90 | 20 |
| Comparative Example 2 | IX | — | — | — | — | — | 100 | — | — | — | 90 | 20 |
| Comparative Example 3 | X | — | — | — | — | 100 | — | — | — | 90 | — | — |

TABLE 2

| | Ratio of cyclization of polyhydroxyamide % | Ratio of Imidization % | Chemical resistance | | Evaluation of degree of elongation | |
|---|---|---|---|---|---|---|
| | | | Variation ratio (%) | Evaluation | Degree of elongation (%) | Evaluation |
| Example 1 | 71 | 75 | 5 | A | 50 | C |
| Example 2 | 96 | 75 | 5 | A | 75 | B |
| Example 3 | 82 | 95 | 15 | B | 62 | C |
| Example 4 | 97 | 98 | 13 | B | 120 | A |
| Example 5 | 96 | 82 | 6 | A | 90 | A |
| Example 6 | 35 | 55 | 20 | B | 80 | A |
| Example 7 | 45 | 80 | 7 | A | 110 | A |
| Example 8 | 92 | 95 | 18 | B | 95 | A |
| Comparative Example 1 | 4 | 31 | Detachment | D | 23 | D |
| Comparative Example 2 | 3 | 35 | Detachment | D | 18 | D |
| Comparative Example 3 | 90 | — | Detachment | D | 91 | A |

This application is based on Japanese Patent Application No. 2016-219464 filed Nov. 10, 2016, and the contents thereof are hereby incorporated by reference.

INDUSTRIAL APPLICABILITY

The present invention can be used preferably in applications for semiconductor apparatus, electronic components such as multilayer wire boards and the like, and organic EL display devices. Specifically, applications for a passivation film of a semiconductor, a surface protective film of a semiconductor device, an interlayer dielectric film, an interlayer dielectric film of a multilayer wire for high-density mounting, an interlayer dielectric film of an electronic component such as an inductor and a SAW filter, a dielectric layer of an organic electroluminescent element (organic EL) are available.

DESCRIPTION OF THE REFERENCE NUMERALS

1 Silicon wafer
2 Al pad
3 Passivation film
4 Dielectric film
5 Metal (Cr, Ti or the like) film
6 Metal wire (Al, Cu or the like)
7 Dielectric film
8 Barrier metal
9 Scribe line
10 Solder bump
11 Encapsulation resin
12 Substrate
13 Dielectric film
14 Dielectric film
15 Metal (Cr, Ti or the like) film
16 Metal wire (Ag, Cu or the like)
17 Metal wire (Ag, Cu or the like)
18 Electrode
19 Encapsulation resin
20 Support substrate (glass substrate, silicon wafer)
21 Electrode pad (Cu)
22 Dielectric film
23 Metal wire (Cu)
24 Cu post
25 Solder bump
26 Semiconductor chip
27 TFT (thin film transistor)
28 Wire
29 TFT Dielectric layer
30 Planarizing layer
31 ITO (transparent electrode)
32 Substrate
33 Contact hole
34 Dielectric layer

The invention claimed is:
1. A di-amine compound represented by the general formula (1):

[Chem 1]

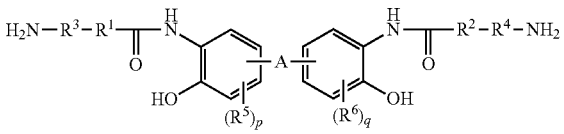

(1)

(wherein in the general formula (1), $R^1$ and $R^2$ each are a divalent aliphatic group;
$R^3$ and $R^4$ each are a divalent aliphatic group, aliphatic ring group, aromatic group, a divalent organic group in which an aromatic group is bonded by —O—, —CO—, —SO$_2$—, —CH$_2$—, —C(CH$_3$)$_2$— or —C(CF$_3$)$_2$— (wherein F is fluorine),
a divalent organic group in which two or more aromatic groups are bonded by a single bond, or a divalent organic group in which two or more aromatic groups are bonded by —O—, —CO—, —SO$_2$—, —CH$_2$—, —C(CH$_3$)$_2$— or —C(CF$_3$)$_2$— (wherein F is fluorine);
$R^5$ and $R^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group;
A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine);

p and q each are an integer number in the range of 0 to 3).

2. The di-amine compound according to claim 1, which is represented by the general formula (1), wherein R$^1$ and R$^2$ in the general formula (1) each are independently a divalent aliphatic group represented by the general formula (2) or the general formula (3),

[Chem 2]

$$H_2N-R^3-R^1-\underset{O}{\overset{H}{\underset{|}{N}}}-\underset{HO}{\overset{}{\bigcirc}}(R^5)_p-A-\underset{OH}{\overset{}{\bigcirc}}(R^6)_q-\underset{O}{\overset{H}{\underset{|}{N}}}-R^2-R^4-NH_2 \quad (1)$$

(wherein in the general formula (1), R$^3$ and R$^4$ each are a divalent aliphatic group, aliphatic ring group, aromatic group,
a divalent organic group in which an aromatic group is bonded by —O—, —CO—, —SO$_2$—, —CH$_2$—, —C(CH$_3$)$_2$— or —C(CF$_3$)$_2$— (wherein F is fluorine),
a divalent organic group in which two or more aromatic groups are bonded by a single bond, or a divalent organic group in which two or more aromatic groups are bonded by —O—, —CO—, —SO$_2$—, —CH$_2$—, —C(CH$_3$)$_2$— or —C(CF$_3$)$_2$— (wherein F is fluorine);
R$^5$ and R$^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group;
A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine);
p and q each are an integer number in the range of 0 to 3),

[Chem 3]

$$*\!-\!(R^7\!-\!O)_a\!-\!(R^8\!-\!O)_b\!-\!(R^9\!-\!O)_c\!-\!R^{10}\!-\!* \quad (2)$$

(wherein in the general formula (2), R$^7$ to R$^{10}$ each are independently a C$_1$-C$_{10}$ alkylene group, and each of a, b and c is an integer number in the range of 1≤a≤20, 0≤b≤20, and 0≤c≤20, and the arrangement of the repeating units may be in a block way or in a random way, and * indicates a chemical bond),

[Chem 4]

$$*\!-\!(\underset{R^{12}}{\overset{R^{11}}{\underset{|}{\overset{|}{C}}}})_n\!-\!* \quad (3)$$

(wherein in the general formula (3), R$^{11}$ and R$^{12}$ each are independently hydrogen, fluorine, or a C$_1$-C$_6$ alkyl group, and n is an integer number of 1 to 20, and * indicates a chemical bond).

3. The di-amine compound according to claim 1, which is represented by the general formula (1), wherein R$^3$ in the general formula (1) is a divalent organic group represented by the formula (4) and R$^4$ in the general formula (1) is a divalent organic group represented by the formula (5),

[Chem 5]

$$H_2N-R^3-R^1-\underset{O}{\overset{H}{\underset{|}{N}}}-\underset{HO}{\overset{}{\bigcirc}}(R^5)_p-A-\underset{OH}{\overset{}{\bigcirc}}(R^6)_q-\underset{O}{\overset{H}{\underset{|}{N}}}-R^2-R^4-NH_2 \quad (1)$$

(wherein in the general formula (1), R$^1$ and R$^2$ each are a divalent aliphatic group,
R$^5$ and R$^6$ each are a hydrogen atom, a halogen atom, a hydroxyl group, a nitro group, a cyano group, an aliphatic group, an aromatic group, an acetyl group, a carboxyl group, or an organic group having any of an ester group, an amide group, an imide group, and a urea group;
A is a divalent aliphatic group, aliphatic ring group, aromatic group, a divalent organic group in which two or more aromatic groups are bonded by a single bond, or a divalent organic group in which two or more aromatic groups are bonded by —O—, —S—, —CO—, —SO$_2$—, —CH$_2$—, —C(CH$_3$)$_2$— or —C(CF$_3$)$_2$— (wherein F is fluorine);
p and q each are an integer number in the range of 0 to 3),

[Chem 6]

$$*-\bigcirc-O-* \quad (4)$$

(wherein in the general formula (4), * indicates a chemical bond,)

[Chem 7]

$$*-O-\bigcirc-* \quad (5)$$

(wherein in the general formula (5), * indicates a chemical bond).

4. A heat-resistant resin having a structure derived from said di-amine compound according to claim 1.

5. The heat-resistant resin according to claim 4, comprising at least one kind selected from the group consisting of polyimides, polyamides, polybenzoxazoles, polybenzimidazoles, polybenzothiazoles, precursors thereof, and copolymers thereof.

6. A resin composition comprising said heat-resistant resin according to claim 4, (b) a photosensitive compound and (c) a solvent.

7. The resin composition according to claim 6, further comprising (d) a compound having two or more of at least one of an alkoxymethyl group and a methylol group.

8. A resin sheet formed of said resin composition according to claim 6.

9. A cured film obtained by curing said resin composition according to claim 6.

10. A cured film obtained by curing said resin sheet of claim 8.

11. A method of producing a relief pattern of a cured film, comprising the steps of coating said resin composition according to claim 6 on a substrate or laminating a resin sheet formed of said resin composition, and drying said resin composition or said resin sheet to form a resin film;
   exposing said resin film through a mask;
   eluting or removing irradiated portion by an alkali solution to develop said resin film; and
   and heat-treating said resin film after the development.

12. The method of producing a relief pattern of a cured film according to claim 11, wherein said step of coating said resin composition on a substrate and drying said resin composition to form said resin film comprises a step of coating said resin composition on a substrate using a slit nozzle.

* * * * *